US011919932B2

(12) United States Patent
Matsushima et al.

(10) Patent No.: US 11,919,932 B2
(45) Date of Patent: *Mar. 5, 2024

(54) HMGN PARTIAL PEPTIDE AND CANCER THERAPY USING THE SAME

(71) Applicants: The University of Tokyo, Tokyo (JP); ONO PHARMACEUTICAL CO., LTD., Osaka (JP); TOKYO UNIVERSITY OF SCIENCE FOUNDATION, Tokyo (JP)

(72) Inventors: Kouji Matsushima, Tokyo (JP); Satoshi Ueha, Tokyo (JP); Shungo Deshimaru, Tokyo (JP); Chang-Yu Chen, Tokyo (JP); Shoji Yokochi, Tokyo (JP); Yoshiro Ishiwata, Tokyo (JP); Shiro Shibayama, Tsukuba (JP)

(73) Assignees: THE UNIVERSITY OF TOKYO, Tokyo (JP); ONO PHARMACEUTICAL CO., LTD., Osaka (JP); TOKYO UNIVERSITY OF SCIENCE FOUNDATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 18/092,737

(22) Filed: Jan. 3, 2023

(65) Prior Publication Data
US 2023/0220022 A1 Jul. 13, 2023

Related U.S. Application Data

(63) Continuation of application No. 16/978,633, filed as application No. PCT/JP2019/009015 on Mar. 7, 2019, now Pat. No. 11,572,393.

(30) Foreign Application Priority Data

Mar. 8, 2018 (JP) ................................ 2018-041560
Jan. 30, 2019 (JP) ................................ 2019-014105

(51) Int. Cl.
*C07K 14/00* (2006.01)
*A61P 35/00* (2006.01)
*C07K 14/47* (2006.01)
*A61K 38/00* (2006.01)

(52) U.S. Cl.
CPC .............. *C07K 14/47* (2013.01); *A61P 35/00* (2018.01); *A61K 38/00* (2013.01)

(58) Field of Classification Search
CPC .......... C07K 14/47; A61P 35/00; A61K 38/00
See application file for complete search history.

(56) References Cited

U.S. PATENT DOCUMENTS 7,544,767 B2  6/2009  Ruoslahti et al.
8,227,417 B2  7/2012  Yang et al.
8,383,613 B2  2/2013  Prendergast et al.
11,572,393 B2* 2/2023  Matsushima ...... C07K 16/2812
2016/0296620 A1 10/2016  Yang et al.

FOREIGN PATENT DOCUMENTS

WO   WO 2011/031477 A2   3/2011
WO   WO 2015/125652 A1   8/2015
WO   WO 2018/047917 A1   3/2018

OTHER PUBLICATIONS

Birger et al., "Increased Tumorigenicity and Sensitivity to Ionizing Radiation upon Loss of Chromosomal Protein HMGN1," Cancer Res (2005), vol. 65, No. 15, pp. 6711-6718.
Chen et al., "Combining an Alarmin HMGN1 Peptide with PD-L1 Blockade Results in Robust Antitumor Effects with a Concomitant Increase of Stem-Like/Progenitor . . . CD8+ T Cells", Cancer Immunol Res, vol. 9, No. 10, Oct. 2021 (Published online First Aug. 3, 2021), pp. 1214-1228 (16 pages total).
Extended European Search Report dated Oct. 20, 2021 for Application No. 19764047.7.
Gerlitz, G., "HMGNs, DNA repair and cancer," Biochimica et Biophysica Acta (2010), vol. 1799, pp. 80-85.
International Search Report dated May 21, 2019, in PCT/JP2019/009015.
Kleponis, J. et al., "Fueling the engin3 and releasing the break: combinational therapy of cancer vaccines and immune checkpoint inhibitors," Cancer Biol. Med. (2015), vol. 12, pp. 201-208.
Nie et al., "Alarmins and Antitumor Immunity," Clinical Therapeutics (2016), vol. 38, No. 5, pp. 1042-1053.
Porkka et al., "A fragment of the HMGN2 protein homes to the nuclei of tumor cells and tumor endothelial cells in vivo," PNAS (May 28, 2002), vol. 99, No. 11, pp. 7444-7449.
Postnikov et al., "Loss of the Nucelosome-Binding Protein HMGN1 Affects the Rate of N-Nitrosodiethylamine-Induced Hepatocarcinogenesis in Mice," Mol. Cancer Res. (Jan. 2014), vol. 12, No. 1, pp. 82-90.
Trieschmann et al., "Modular Structure of Chromosomal Proteins HMG-14 and HMG-17: Definition of a Transcriptional Enhancement Domain Distinct from the Nucleosomal Binding Domain," Molecular and Cellular Biology (Dec. 1995), vol. 15, No. 12, pp. 6663-6669.
Wei et al., "The Alarmin HMGN1 Contributes to Antitumor Immunity and Is a Potent Immunoadjuvant," Cancer Res. (2014), vol. 74, No. 21, pp. 5989-5998.

(Continued)

*Primary Examiner* — Jeanette M Lieb
(74) *Attorney, Agent, or Firm* — Birch, Stewart, Kolasch & Birch, LLP

(57) ABSTRACT

Disclosed are a novel therapeutic means effective and practical against cancer, and a novel substance useful as such a therapeutic means. Provided are novel peptides derived from a partial region of HMGN1, HMGN2, HMGN4 or HMGN5, and anti-cancer agents and anti-cancer effect enhancers containing the peptide as an active ingredient. The peptide of the present invention has an anti-tumor effect even independently, and exerts a remarkably excellent anti-tumor effect particularly when used in combination with an immune checkpoint regulator, or an anti-CD4 antibody or antigen-binding fragment thereof.

18 Claims, 14 Drawing Sheets

Specification includes a Sequence Listing.

(56) References Cited

OTHER PUBLICATIONS

Yang et al., "Harnessing the alarmin HMGN1 for anticancer therapy," Immunotherapy (2015), vol. 7, No. 11, pp. 1129-1131.

\* cited by examiner

```
                                SEQUENCE LISTING

Sequence total quantity: 18
SEQ ID NO: 1           moltype = AA  length = 37
FEATURE                Location/Qualifiers
REGION                 1..37
                       note = mouse HMGN1 NBD-peptide 1 (mPep1)
source                 1..37
                       mol_type = protein
                       organism = synthetic construct
SEQUENCE: 1
SADGAAKAEP KRRSARLSAK PAPAKVDAKP KKAAGKD                                  37

SEQ ID NO: 2           moltype = AA  length = 40
FEATURE                Location/Qualifiers
REGION                 1..40
                       note = mouse HMGN1 NBD-peptide 2 (mPep2)
source                 1..40
                       mol_type = protein
                       organism = synthetic construct
SEQUENCE: 2
VQIKGKRGAK GKQADVADQQ TTELPAENGE TENQSPASEE                               40

SEQ ID NO: 3           moltype = AA  length = 37
FEATURE                Location/Qualifiers
REGION                 1..37
                       note = Human HMGN1 NBD-peptide 1 (Pep1)
source                 1..37
                       mol_type = protein
                       organism = synthetic construct
SEQUENCE: 3
SSAEGAAKEE PKRRSARLSA KPPAKVEAKP KKAAAKD                                  37

SEQ ID NO: 4           moltype = AA  length = 24
FEATURE                Location/Qualifiers
REGION                 1..24
                       note = Human HMGN1 NBD-peptide 1 delta-C (Pep1 delta-C)
source                 1..24
                       mol_type = protein
                       organism = synthetic construct
SEQUENCE: 4
SSAEGAAKEE PKRRSARLSA KPPA                                                24
```

```
SEQ ID NO: 5              moltype = AA   length = 32
FEATURE                   Location/Qualifiers
REGION                    1..32
                          note = Human HMGN1 NBD-peptide 1 delta-C1 (Pep1 delta-C1)
source                    1..32
                          mol_type = protein
                          organism = synthetic construct
SEQUENCE: 5
SSAEGAAKEE PKRRSARLSA KPPAKVEAKP KK                                         32

SEQ ID NO: 6              moltype = AA   length = 28
FEATURE                   Location/Qualifiers
REGION                    1..28
                          note = Human HMGN1 NBD-peptide 1 delta-C2 (Pep1 delta-C2)
source                    1..28
                          mol_type = protein
                          organism = synthetic construct
SEQUENCE: 6
SSAEGAAKEE PKRRSARLSA KPPAKVEA                                              28

SEQ ID NO: 7              moltype = AA   length = 32
FEATURE                   Location/Qualifiers
REGION                    1..32
                          note = Human HMGN1 NBD-peptide 1 delta-N1 (Pep1 delta-N1)
source                    1..32
                          mol_type = protein
                          organism = synthetic construct
SEQUENCE: 7
AAKEEPKRRS ARLSAKPPAK VEAKPKKAAA KD                                         32

SEQ ID NO: 8              moltype = AA   length = 28
FEATURE                   Location/Qualifiers
REGION                    1..28
                          note = Human HMGN1 NBD-peptide 1 delta-N2 (Pep1 delta-N2)
source                    1..28
                          mol_type = protein
                          organism = synthetic construct
SEQUENCE: 8
EPKRRSARLS AKPPAKVEAK PKKAAAKD                                              28

SEQ ID NO: 9              moltype = AA   length = 23
FEATURE                   Location/Qualifiers
REGION                    1..23
                          note = Human HMGN1 NBD-peptide 1 delta-N3 (Pep1 delta-N3)
source                    1..23
                          mol_type = protein
                          organism = synthetic construct
SEQUENCE: 9
SARLSAKPPA KVEAKPKKAA AKD                                                   23

SEQ ID NO: 10             moltype = AA   length = 36
FEATURE                   Location/Qualifiers
REGION                    1..36
                          note = Human HMGN1 peptide O (PepO)
source                    1..36
                          mol_type = protein
                          organism = synthetic construct
SEQUENCE: 10
KEEPKRRSAR LSAKPPAKVE AKPKKAAAKD KSSDKK                                     36

SEQ ID NO: 11             moltype = AA   length = 36
FEATURE                   Location/Qualifiers
REGION                    1..36
                          note = Human HMGN1 NBD-peptide 1 mutant (Pep1 mutant)
source                    1..36
                          mol_type = protein
                          organism = synthetic construct
SEQUENCE: 11
SAEGAAKEEP KDDSADLSAK PPAKVEAKPK KAAAKD                                     36

SEQ ID NO: 12             moltype = AA   length = 44
FEATURE                   Location/Qualifiers
REGION                    1..44
                          note = Human HMGN2 NBD-peptide (N2Pep)
source                    1..44
                          mol_type = protein
                          organism = synthetic construct
SEQUENCE: 12
```

```
EGDAKGDKAK VKDEPQRRSA RLSAKPAPPK PEPKPKKAPA KKGE                   44

SEQ ID NO: 13          moltype = AA   length = 46
FEATURE                Location/Qualifiers
REGION                 1..46
                       note = Human HMGN3 NBD-peptide (N3Pep)
source                 1..46
                       mol_type = protein
                       organism = synthetic construct
SEQUENCE: 13
SPENTEGKDG SKVTKQEPTR RSARLSAKPA PPKPEPKPRK TSAKKE                 46

SEQ ID NO: 14          moltype = AA   length = 43
FEATURE                Location/Qualifiers
REGION                 1..43
                       note = Human HMGN4 NBD-peptide (N4Pep)
source                 1..43
                       mol_type = protein
                       organism = synthetic construct
SEQUENCE: 14
GDAKGDKAKV KDEPQRRSAR LSAKPAPPKP EPRPKKASAK KGE                    43

SEQ ID NO: 15          moltype = AA   length = 43
FEATURE                Location/Qualifiers
REGION                 1..43
                       note = Human HMGN5 NBD-peptide (N5Pep)
source                 1..43
                       mol_type = protein
                       organism = synthetic construct
SEQUENCE: 15
GQGDMRQEPK RRSARLSAML VPVTPEVKPK RTSSSRKMKT KSD                    43

SEQ ID NO: 16          moltype = AA   length = 96
FEATURE                Location/Qualifiers
source                 1..96
                       mol_type = protein
                       organism = Mus musculus
SEQUENCE: 16
MPKRKVSADG AAKAEPKRRS ARLSAKPAPA KVDAKPKKAA GKDKASDKKV QIKGKRGAKG   60
KQADVADQQT TELPAENGET ENQSPASEEE KEAKSD                            96

SEQ ID NO: 17          moltype = AA   length = 100
FEATURE                Location/Qualifiers
source                 1..100
                       mol_type = protein
                       organism = Homo sapiens
SEQUENCE: 17
MPKRKVSSAE GAAKEEPKRR SARLSAKPPA KVEAKPKKAA AKDKSSDKKV QTKGKRGAKG   60
KQAEVANQET KEDLPAENGE TKTEESPASD EAGEKEAKSD                        100

SEQ ID NO: 18          moltype = AA   length = 23
FEATURE                Location/Qualifiers
REGION                 1..23
                       note = Human HMGN1 NBD-peptide1 core (Pep1core)
source                 1..23
                       mol_type = protein
                       organism = synthetic construct
SEQUENCE: 18
EPKRRSARLS AKPPAKVEAK PKK                                          23
```

HMGN PARTIAL PEPTIDE AND CANCER THERAPY USING THE SAME

CROSS-REFERENCE TO RELATED APPLICATIONS

This application is a Continuation of co-pending application Ser. No. 16/978,633, filed on Sep. 4, 2020, which is the National Phase under 35 U.S.C. § 371 of International Application No. PCT/JP2019/009015, filed on Mar. 7, 2019, which claims the benefit under 35 U.S.C. § 119(a) to Patent Application No. 2018-041560, filed in Japan on Mar. 8, 2018 and Patent Application No. 2019-014105, filed in Japan on Jan. 30, 2019, all of which are hereby expressly incorporated by reference into the present application.

REFERENCE TO ELECTRONIC SEQUENCE LISTING

This application contains a Sequence Listing which has been submitted electronically in .XML format and is hereby incorporated by reference in its entirety. Said .XML copy, created on Dec. 23, 2022, is named "2023-01-03_Sequence_Listing_0760-0524PUS2.xml" and is 23,164 bytes in size. The sequence listing contained in this .XML file is part of the specification and is hereby incorporated by reference herein in its entirety.

The present invention relates to novel peptides and a cancer therapy using the same. More specifically, the present invention relates to peptides derived from a partial region of HMGN1, 2, 4 or 5, and a cancer therapy using a combination of the peptide and an immune checkpoint regulator or an anti-CD4 antibody.

BACKGROUND ART

HMG proteins are a superfamily of nucleosome-binding proteins and are classified into HMGA, HMGB and HMGN families. These polypeptides regulate gene expression by binding to DNA. In addition, HMG proteins are released extracellularly by cell death such as necrosis induced by infection or injury, or by a pathway that does not pass through a normal transport pathway, an endoplasmic reticulum-Golgi apparatus pathway, and induces an inflammatory response, so that it is classified into an alarmin (alarmin) molecular group. Other known alarmin proteins include cytokines such as IL-la and IL-33, HSP (heat shock protein), 5100 proteins, and the like. The alarmin proteins are also involved in recognition of a pattern structure (pathogen-associated molecular patterns:PAMPs) inherent to a pathogen via a pattern recognition receptor represented by Toll-like receptor (TLR).

HMGN, which is one of the families of HMG proteins, has five types, HMGN1, HMGN2, HMGN3, HMGN4, and HMGN5. Among them, with regard to HMGN1, it has been reported that tumor development is increased in HMGN1-deficient mice (for example, Non Patent Literatures 1 to 3), and it has been reported that HMGN1 is a booster of anti-tumor immunity, and an HMGN1 protein can be used in combination with the conventional cancer therapy such as surgery, chemotherapy or radiation therapy, an immune checkpoint inhibitor, or the like (Non Patent Literature 4).

However, all of these reports are reports relating to the possibility of application of a full-length HMGN1 protein to cancer treatment, or a relationship between a full-length HMGN1 protein and tumor development in vivo. Patent Literature 1 discloses an invention in which a partial peptide of HMGN2 is used for treating cancer, but it is an invention of using the partial peptide of HMGN2 as a carrier for an anti-cancer agent by utilizing the fact that it easily accumulates in tumor blood vessels, and does not mean that the partial peptide of HMGN2 has an anti-tumor effect. Further, Patent Literature 2 discloses use of HMGN peptides or functional fragments thereof for enhancing an antigen-specific immune reaction, but does not disclose a specific anti-tumor action.

CITATIONS LIST

Patent Literature 1: U.S. Pat. No. 7,544,767
Patent Literature 2: U.S. Pat. No. 8,227,417
Non Patent Literature 1: Birger et al., "Increased Tumorigenicity and Sensitivity to Ionizing Radiation upon Loss of Chromosomal Protein HMGN1." Cancer Research, 65: (15). Aug. 1, 2005, p. 6711-6718
Non Patent Literature 2: Gabi Gerlitz, "HMGNs, DNA Repair and Cancer." Biochim Biophys Acta. 2010; 1799(1-2):80-85.
Non Patent Literature 3: Postnikov et al., "Loss of the nucleosome-binding protein HMGN1 affects the rate of N-nitrosodiethylamine induced hepatocarcinogenesis in mice." Mol Cancer Res. 2014 January; 12(1):82-90.
Non Patent Literature 4: De Yang, Michael Bustin and Joost J Oppenheim, "Harnessing the alarmin HMGN1 for anticancer therapy." Immunotherapy, 2015; 7(11):1129-31. Published Online:16 Nov. 2015

SUMMARY OF INVENTION

Technical Problems

An object of the present invention is to provide a novel therapeutic means effective and practical against cancer, and a novel substance useful as such a therapeutic means.

Solutions to Problems

The present inventors have intensively studied anti-tumor effects of partial peptides of HMGN using tumor-bearing model mice, and consequently found that, in the tumor-bearing model mice, novel partial peptides containing a specific region of HMGN1 significantly suppress proliferation of tumor even in single administration, and a synergistic anti-tumor effect is obtained by a combined use with an immune checkpoint regulator, and further found that novel partial peptides containing a specific region of HMGN2, HMGN4, and HMGN5 also have an anti-tumor effect similar to the HMGN1 partial peptides, and the novel partial peptides according to the invention of the present application have a remarkably high anti-tumor effect as compared with the partial peptides disclosed in Patent Literature 2, thereby completing the invention of the present application.

More specifically, the present invention provides a peptide whose amino acid sequence is represented by any one amino acid sequence selected from the following (1) to (9):

(1)
(SEQ ID NO: 3)
SSAE GAAKEEPKRR SARLSAKPPA KVEAKPKKAA AKD (2) an amino acid sequence in which 1 to 8 amino acid residues at the C terminus are deleted in (1)

(3) an amino acid sequence in which 1 to 13 amino acid residues at the N terminus are deleted in (1)

(4) an amino acid sequence in which 1 to 13 amino acid residues at the N terminus are deleted in (2)

(5)
(SEQ ID NO: 12)
EGDAKGDK AKVKDEPQRR SARLSAKPA PPKPEPKPKKAPAKKGE (6)
(SEQ ID NO: 14)
GDAKGDK AKVKDEPQRR SARLSAKPA PPKPEPRPKKASAKKGE (7)
(SEQ ID NO: 15)
GQG DMRQEPKRR SARLSAMLV PVTPEVKPKRTSSSRKMKTKSD (8) an amino acid sequence in which 1 to 5 amino acid residues at the C terminus and/or 1 to 5 amino acid residues at the N terminus are deleted in any one of (5) to (7)

(9) an amino acid sequence in which 1 to 3 amino acid residues are substituted in any one of (1) to (8).

A preferred example of (9) is,

(10) an amino acid sequence in which 1 to 3 amino acid residues are substituted in any one of (1) to (4).

The present invention also provides an anti-cancer agent containing at least one peptide as an active ingredient, in which an amino acid sequence of the at least one peptide is represented by any one of the following (1) to (9):

(1)
(SEQ ID NO: 3)
SSAE GAAKEEPKRR SARLSAKPPA KVEAKPKKAA AKD (2) an amino acid sequence in which 1 to 8 amino acid residues at the C terminus are deleted in (1)

(3) an amino acid sequence in which 1 to 13 amino acid residues at the N terminus are deleted in (1)

(4) an amino acid sequence in which 1 to 13 amino acid residues at the N terminus are deleted in (2)

(5)
(SEQ ID NO: 12)
EGDAKGDK AKVKDEPQRR SARLSAKPA PPKPEPKPKKAPAKKGE (6)
(SEQ ID NO: 14)
GDAKGDK AKVKDEPQRR SARLSAKPA PPKPEPRPKKASAKKGE (7)
(SEQ ID NO: 15)
GQG DMRQEPKRR SARLSAMLV PVTPEVKPKRTSSSRKMKTKSD (8) an amino acid sequence in which 1 to 5 amino acid residues at the C terminus and/or 1 to 5 amino acid residues at the N terminus are deleted in any one of (5) to (7)

(9) an amino acid sequence in which 1 to 3 amino acid residues are substituted in any one of (1) to (8).

A preferred example of (9) is,

(10) an amino acid sequence in which 1 to 3 amino acid residues are substituted in any one of (1) to (4).

Further, the present invention provides an anti-cancer effect enhancer for an anti-cancer agent, containing at least one peptide, in which an amino acid sequence of the at least one peptide is represented by any one of the following (1) to (9):

(1)
(SEQ ID NO: 3)
SSAE GAAKEEPKRR SARLSAKPPA KVEAKPKKAA AKD (2) an amino acid sequence in which 1 to 8 amino acid residues at the C terminus are deleted in (1)

(3) an amino acid sequence in which 1 to 13 amino acid residues at the N terminus are deleted in (1)

(4) an amino acid sequence in which 1 to 13 amino acid residues at the N terminus are deleted in (2)

(5)
(SEQ ID NO: 12)
EGDAKGDK AKVKDEPQRR SARLSAKPA PPKPEPKPKKAPAKKGE (6)
(SEQ ID NO: 14)
GDAKGDK AKVKDEPQRR SARLSAKPA PPKPEPRPKKASAKKGE (7)
(SEQ ID NO: 15)
GQG DMRQEPKRR SARLSAMLV PVTPEVKPKRTSSSRKMKTKSD (8) an amino acid sequence in which 1 to 5 amino acid residues at the C terminus and/or 1 to 5 amino acid residues at the N terminus are deleted in any one of (5) to (7)

(9) an amino acid sequence in which 1 to 3 amino acid residues are substituted in any one of (1) to (8).

A preferred example of (9) is,

(10) an amino acid sequence in which 1 to 3 amino acid residues are substituted in any one of (1) to (4).

Furthermore, the present invention provides a method of treating cancer, including administering an effective amount of the peptide of the present invention to a patient in need of treatment of cancer.

The following is included as an embodiment of the present invention.

[1] A peptide whose amino acid sequence is represented by any one amino acid sequence selected from the following (1) to (9):

(1)
(SEQ ID NO: 3)
SSAE GAAKEEPKRR SARLSAKPPA KVEAKPKKAA AKD (2) an amino acid sequence in which 1 to 8 amino acid residues at the C terminus are deleted in (1)

(3) an amino acid sequence in which 1 to 13 amino acid residues at the N terminus are deleted in (1)

(4) an amino acid sequence in which 1 to 13 amino acid residues at the N terminus are deleted in (2)

(5)
(SEQ ID NO: 12)
EGDAKGDK AKVKDEPQRR SARLSAKPA PPKPEPKPKKAPAKKGE (6)
(SEQ ID NO: 14)
GDAKGDK AKVKDEPQRR SARLSAKPA PPKPEPRPKKASAKKGE (7)
(SEQ ID NO: 15)
GQG DMRQEPKRR SARLSAMLV PVTPEVKPKRTSSSRKMKTKSD (8) an amino acid sequence in which 1 to 5 amino acid residues at the C terminus and/or 1 to 5 amino acid residues at the N terminus are deleted in any one of (5) to (7)

(9) an amino acid sequence in which 1 to 3 amino acid residues are substituted in any one of (1) to (8).

[2] The peptide according to the [1], in which the (2) is an amino acid sequence in which 1 to 5 amino acid residues at the C terminus are deleted in (1), the (3) is an amino acid sequence in which 1 to 9 amino acid residues at the N terminus are deleted in (1), and the (4) is an amino acid sequence in which 1 to 9 amino acid residues at the N terminus are deleted in (2).

[3] The peptide according to the [1] or [2], whose amino acid sequence is represented by any one of the (1) to (7).

[4] The peptide according to the [1] or [2], whose amino acid sequence is represented by any one of the (1) to (3) and (5) to (7).

[5] The peptide according to any one of the [1] to [3], in which the (2) is SSAE GAAKEEPKRR SARLSAKPPA KVEAKPKK (SEQ ID NO: 5), the (3) is AAKEEPKRR SARLSAKPPA KVEAKPKKAAAKD (SEQ ID NO: 7) or EPKRR SARLSAKPPA KVEAKPKKAA AKD (SEQ ID NO: 8), and the (4) is EPKRR SARLSAKPPA KVEAKPKK (SEQ ID NO: 18).

[6] The peptide according to any one of the [1] to [4], in which the (2) is SSAE GAAKEEPKRR SARLSAKPPA KVEAKPKK (SEQ ID NO: 5), and the (3) is AAKEEPKRR SARLSAKPPA KVEAKPKKAA AKD (SEQ ID NO: 7) or EPKRR SARLSAKPPA KVEAKPKKAAAKD (SEQ ID NO: 8).

[7] The peptide according to the [1], whose amino acid sequence is represented by any amino acid sequence selected from SEQ ID NO: 3, SEQ ID NO: 5, SEQ ID NO: 7, SEQ ID NO: 8, SEQ ID NO: 12, SEQ ID NO: 14, SEQ ID NO: 15, and SEQ ID NO: 18.

[8] The peptide according to the [1], whose amino acid sequence is represented by any amino acid sequence selected from SEQ ID NO: 3, SEQ ID NO: 5, SEQ ID NO: 7, SEQ ID NO: 8, SEQ ID NO: 12, SEQ ID NO: 14, and SEQ ID NO: 15.

[9] The peptide according to any one of the [1] to [8], which is an anti-cancer active peptide.

[10] The peptide according to any one of the [1] to [8], which is an anti-cancer effect-enhancing peptide.

[11] An anti-cancer agent containing at least one peptide as an active ingredient, for use in combination with at least one selected from an immune checkpoint regulator and an anti-CD4 antibody or antigen-binding fragment thereof, in which an amino acid sequence of the at least one peptide is represented by any one of the following (1) to (9):

(1)
(SEQ ID NO: 3)
SSAE GAAKEEPKRR SARLSAKPPA KVEAKPKKAA AKD (2) an amino acid sequence in which 1 to 8 amino acid residues at the C terminus are deleted in (1)

(3) an amino acid sequence in which 1 to 13 amino acid residues at the N terminus are deleted in (1)

(4) an amino acid sequence in which 1 to 13 amino acid residues at the N terminus are deleted in (2)

(5)
(SEQ ID NO: 12)
EGDAKGDK AKVKDEPQRR SARLSAKPA PPKPEPKPKKAPAKKGE (6)
(SEQ ID NO: 14)
GDAKGDK AKVKDEPQRR SARLSAKPA PPKPEPRPKKASAKKGE (7)
(SEQ ID NO: 15)
GQG DMRQEPKRR SARLSAMLV PVTPEVKPKRTSSSRKMKTKSD (8) an amino acid sequence in which 1 to 5 amino acid residues at the C terminus and/or 1 to 5 amino acid residues at the N terminus are deleted in any one of (5) to (7)

(9) an amino acid sequence in which 1 to 3 amino acid residues are substituted in any one of (1) to (8).

[12] The anti-cancer agent according to the [11], in which the (2) is an amino acid sequence in which 1 to 5 amino acid residues at the C terminus are deleted in (1), the (3) is an amino acid sequence in which 1 to 9 amino acid residues at the N terminus are deleted in (1), and the (4) is an amino acid sequence in which 1 to 9 amino acid residues at the N terminus are deleted in (2).

[13] The anti-cancer agent according to the [11] or [12], in which the amino acid sequence of the at least one peptide is represented by any one of the (1) to (7).

[14] The anti-cancer agent according to the [11] or [12], in which the amino acid sequence of the at least one peptide is represented by any one of the (1) to (3) and (5) to (7).

[15] The anti-cancer agent according to any one of the [11] to [13], in which the (2) is SSAE GAAKEEPKRR SARLSAKPPA KVEAKPKK (SEQ ID NO: 5), the (3) is AAKEEPKRR SARLSAKPPA KVEAKPKKAAAKD (SEQ ID NO: 7) or EPKRR SARLSAKPPA KVEAKPKKAAAKD (SEQ ID NO: 8), and the (4) is EPKRR SARLSAKPPA KVEAKPKK (SEQ ID NO: 18).

[16] The anti-cancer agent according to any one of the [11] to [14], in which the (2) is SSAE GAAKEEPKRR SARLSAKPPA KVEAKPKK (SEQ ID NO: 5), and the (3) is AAKEEPKRR SARLSAKPPA KVEAKPKKAAAKD (SEQ ID NO: 7) or EPKRR SARLSAKPPA KVEAKPKKAAAKD (SEQ ID NO: 8).

[17] The anti-cancer agent according to the [11], in which the amino acid sequence of the at least one peptide is represented by any amino acid sequence selected from SEQ ID NO: 3, SEQ ID NO: 5, SEQ ID NO: 7, SEQ ID NO: 8, SEQ ID NO: 12, SEQ ID NO: 14, SEQ ID NO: 15, and SEQ ID NO: 18.

[18] The anti-cancer agent according to the [11], in which the amino acid sequence of the at least one peptide is represented by any amino acid sequence selected from SEQ ID NO: 3, SEQ ID NO: 5, SEQ ID NO: 7, SEQ ID NO: 8, SEQ ID NO: 12, SEQ ID NO: 14, and SEQ ID NO: 15.

[19] The anti-cancer agent according to the [11] to [18], in which the immune checkpoint regulator is at least one selected from antagonists against inhibitory immune checkpoint molecules, and agonists against co-stimulatory immune checkpoint molecules.

[20] The anti-cancer agent according to the [19], in which the immune checkpoint regulator is at least one anti-immune checkpoint antibody.

[21] The anti-cancer agent according to the [20], in which the anti-immune checkpoint antibody is at least one selected from an antagonistic anti-PD-1 antibody, an anti-PD-L1 antibody, and an anti-PD-L2 antibody.

[22] The anti-cancer agent according to the [11] to [21], in which the anti-CD4 antibody or antigen-binding fragment thereof is an anti-CD4 antibody having cytotoxic activity, or an anti-CD4 antibody or antigen-binding fragment to which a cytotoxic component is bound.

[23] The anti-cancer agent according to any one of the [11] to [22], in which the cancer is a solid cancer.

[24] The anti-cancer agent according to any one of the [11] to [18], in which the peptide is an anti-cancer active peptide.

[25] An anti-cancer effect enhancer for an anti-cancer agent, containing at least one peptide, in which the anti-cancer agent is an anti-cancer agent containing at least one selected from an immune checkpoint regulator and an anti-CD4 antibody or antigen-binding fragment thereof as an active ingredient, and an amino acid sequence of the at least one peptide is represented by any one of the following (1) to (9):

(1)
(SEQ ID NO: 3)
SSAE GAAKEEPKRR SARLSAKPPA KVEAKPKKAA AKD (2) an amino acid sequence in which 1 to 8 amino acid residues at the C terminus are deleted in (1)
(3) an amino acid sequence in which 1 to 13 amino acid residues at the N terminus are deleted in (1)
(4) an amino acid sequence in which 1 to 13 amino acid residues at the N terminus are deleted in (2)

(5)
(SEQ ID NO: 12)
EGDAKGDK AKVKDEPQRR SARLSAKPA PPKPEPKPKKAPAKKGE (6)
(SEQ ID NO: 14)
GDAKGDK AKVKDEPQRR SARLSAKPA PPKPEPRPKKASAKKGE (7)
(SEQ ID NO: 15)
GQG DMRQEPKRR SARLSAMLV PVTPEVKPKRTSSSRKMKTKSD (8) an amino acid sequence in which 1 to 5 amino acid residues at the C terminus and/or 1 to 5 amino acid residues at the N terminus are deleted in any one of (5) to (7)
(9) an amino acid sequence in which 1 to 3 amino acid residues are substituted in any one of (1) to (8).

[26] The anti-cancer effect enhancer according to the [25], in which the peptide is an anti-cancer effect-enhancing peptide.

[27] The peptide according to any one of the [1] to [3], whose amino acid sequence is represented by any one of the (1) to (4).

An anti-cancer agent containing at least one peptide as an active ingredient, in which an amino acid sequence of the at least one peptide is represented by any one of the following (1) to (9):

(1)
(SEQ ID NO: 3)
SSAE GAAKEEPKRR SARLSAKPPA KVEAKPKKAA AKD (2) an amino acid sequence in which 1 to 8 amino acid residues at the C terminus are deleted in (1)
(3) an amino acid sequence in which 1 to 13 amino acid residues at the N terminus are deleted in (1)
(4) an amino acid sequence in which 1 to 13 amino acid residues at the N terminus are deleted in (2)

(5)
(SEQ ID NO: 12)
EGDAKGDK AKVKDEPQRR SARLSAKPA PPKPEPKPKKAPAKKGE (6)
(SEQ ID NO: 14)
GDAKGDK AKVKDEPQRR SARLSAKPA PPKPEPRPKKASAKKGE (7)
(SEQ ID NO: 15)
GQG DMRQEPKRR SARLSAMLV PVTPEVKPKRTSSSRKMKTKSD (8) an amino acid sequence in which 1 to 5 amino acid residues at the C terminus and/or 1 to 5 amino acid residues at the N terminus are deleted in any one of (5) to (7)
(9) an amino acid sequence in which 1 to 3 amino acid residues are substituted in any one of (1) to (8).

[29] An anti-cancer effect enhancer for an anti-cancer agent, containing at least one peptide, in which an amino acid sequence of the at least one peptide is represented by any one of the following (1) to (9):

(1)
(SEQ ID NO: 3)
SSAE GAAKEEPKRR SARLSAKPPA KVEAKPKKAA AKD (2) an amino acid sequence in which 1 to 8 amino acid residues at the C terminus are deleted in (1)
(3) an amino acid sequence in which 1 to 13 amino acid residues at the N terminus are deleted in (1)
(4) an amino acid sequence in which 1 to 13 amino acid residues at the N terminus are deleted in (2)

(5)
(SEQ ID NO: 12)
EGDAKGDK AKVKDEPQRR SARLSAKPA PPKPEPKPKKAPAKKGE (6)
(SEQ ID NO: 14)
GDAKGDK AKVKDEPQRR SARLSAKPA PPKPEPRPKKASAKKGE (7)
(SEQ ID NO: 15)
GQG DMRQEPKRR SARLSAMLV PVTPEVKPKRTSSSRKMKTKSD (8) an amino acid sequence in which 1 to 5 amino acid residues at the C terminus and/or 1 to 5 amino acid residues at the N terminus are deleted in any one of (5) to (7)
(9) an amino acid sequence in which 1 to 3 amino acid residues are substituted in any one of (1) to (8).

[30] An anti-cancer agent containing the peptide according to any one of the [1] to [10] or [27] as an active ingredient.

[31] An anti-cancer agent containing an amino acid sequence of the peptide according to any one of the [1] to [10] or [27].

[32] The anti-cancer agent according to the [30] or [31], for use in combination with at least one selected from an immune checkpoint regulator and an anti-CD4 antibody or antigen-binding fragment thereof.

[33] An anti-cancer effect enhancer for an anti-cancer agent, containing the peptide according to any one of the [1] to [10] or [27].

[34] An anti-cancer effect enhancer for an anti-cancer agent, containing an amino acid sequence of the peptide according to any one of the [1] to [10] or [27].

[35] The anti-cancer effect enhancer according to the [33] or [34], in which the anti-cancer agent is an anti-cancer agent containing at least one selected from an immune checkpoint regulator and an anti-CD4 antibody or antigen-binding fragment thereof as an active ingredient.

[36] The anti-cancer agent according to the [32] or the anti-cancer effect enhancer according to the [35], in which the immune checkpoint regulator is at least one selected from an antagonist against an inhibitory immune checkpoint molecule, and an agonist against a co-stimulatory immune checkpoint molecule.

[37] The agent according to the [36], in which the immune checkpoint regulator is at least one anti-immune checkpoint antibody.

[38] The agent according to the [37], in which the anti-immune checkpoint antibody is at least one selected from an antagonistic anti-PD-1 antibody, an anti-PD-L1 antibody, and an anti-PD-L2 antibody.

[39] The agent according to any one of the [32], and [35] to [38], in which the anti-CD4 antibody or antigen-binding fragment thereof is an anti-CD4 antibody having cytotoxic activity, or an anti-CD4 antibody or antigen-binding fragment to which a cytotoxic component is bound.

[40] The agent according to any one of the [30] to [39], in which the cancer is a solid cancer.

[41] A pharmaceutical composition containing the peptide according to any one of the [1] to [10] or [27] as an active ingredient.

[42] A pharmaceutical composition containing the peptide having the amino acid sequence as an active part according to any one of the [1] to [10] or [27].

[43] A pharmaceutical composition containing an amino acid sequence of the peptide according to any one of the [1] to [10] or [27].

[44] A method of treating cancer, including administering an effective amount of the peptide according to any one of the [1] to [10] or [27] to a patient in need of treatment of cancer.

[45] The peptide according to any one of the [1] to [10] or [27], which is used for cancer treatment.

[46] A use of the peptide according to any one of the [1] to [10] or [27] for producing an anti-cancer agent.

Advantageous Effects of Invention

The present invention provides novel peptides derived from each of partial regions of HMGN1, HMGN2, HMGN4, and HMGN5, and a novel cancer therapy using these peptides. The anti-cancer agent containing the peptide of the present invention is used alone or in combination with at least one selected from an immune checkpoint regulator and an anti-CD4 depleting antibody, and an anti-CD4 antibody or antigen-binding fragment thereof to which a cytotoxic component is bound, thereby exerting a remarkably excellent anti-tumor effect. The effect is as shown in the following examples, and the anti-tumor effect has been confirmed to the extent that multiple complete tumor regression cases appear. The anti-tumor effect of the novel peptide of the present invention can be also regarded as an effect of enhancing the anti-cancer effect. For example, it can be also regarded as an effect of enhancing the anti-cancer effect of anti-cancer agents such as immune checkpoint regulators and anti-CD4 depleting antibodies. Since the peptide of the present invention has a length of several tens of residues, it can be easily prepared by chemical synthesis. In the case of chemical synthesis, unlike gene recombination, components derived from host cells are not contaminated, which is advantageous as a pharmaceutical. From the results of the following examples, it is suggested that blood half-life of the peptide of the present invention is similar to that of the original full-length HMGN protein, and it can also be mentioned as an advantage of the present invention.

BRIEF DESCRIPTION OF DRAWINGS

FIG. 1-2 shows time-dependent changes in tumor volume for each individual mouse in each group of Colon26 tumor-bearing mice administered with a mouse full-length HMGN1 protein (mHMGN1), and two partial peptides thereof (mPep1, mPep2) alone or in combination with an anti-PD-L1 antibody (200 μg/mouse). The HMGN1 protein and partial peptides were administered at the doses shown in the figure.

FIG. 2 shows measurement results of tumor volume 24 days after tumor cell implantation in each group of Colon26 tumor-bearing mice administered with a mouse full-length HMGN1 protein, and two partial peptides thereof (mPep1, mPep2) alone or in combination with an anti-PD-L1 antibody (200 μg/mouse). The HMGN1 protein and partial peptides were administered at the doses shown in the figure. Significant difference from the control group *: $p<0.05$, **: $p<0.01$ (Dunnett).

FIG. 4-1 shows time-dependent changes in tumor volume for each individual mouse in a Pep1 single administration group and a Pep1+anti-PD-L1 antibody combination group. Pep1 was administered at the dose (ng/mouse) shown in the figure. The anti-PD-L1 antibody was administered at 200 μg/mouse.

FIG. 4-2 shows time-dependent changes in tumor volume for each individual mouse in a Pep1 single administration group and a Pep1+anti-PD-L1 antibody combination group. Pep1 was administered at the dose (ng/mouse) shown in the figure. The anti-PD-L1 antibody was administered at 200 μg/mouse.

FIG. 5-1 shows time-dependent changes in tumor volume for each individual mouse in each group of Colon26 tumor-bearing mice administered with various terminally deleted forms and R→D substitutions of Pep1, each in combination with an anti-PD-L1 antibody (200 μg/mouse). Each peptide was administered at the dose (ng/mouse) shown in the figure.

FIG. 5-2 shows time-dependent changes in tumor volume for each individual mouse in each group of Colon26 tumor-bearing mice administered with various terminally deleted forms and R→D substitutions of Pep1, each in combination with an anti-PD-L1 antibody (200 μg/mouse). Each peptide was administered at the dose (ng/mouse) shown in the figure.

FIG. 7-1 shows time-dependent changes in tumor volume for each individual mouse in each group of Colon26 tumor-bearing mice in which Pep1core was administered in combination with an anti-PD-L1 antibody (200 μg/mouse). For comparison, the time-dependent changes in tumor volume of the Pep1+anti-PD-L1 antibody combination group, the Pep1 ΔC1+anti-PD-L1 antibody combination group and the Pep1ΔN2+anti-PD-L1 antibody combination group are also shown. Each peptide was administered at the dose (ng/mouse) shown in the figure.

FIG. 7-2 shows time-dependent changes in tumor volume for each individual mouse in each group of Colon26 tumor-bearing mice in which Pep1core was administered in combination with an anti-PD-L1 antibody (200 µg/mouse). For comparison, the time-dependent changes in tumor volume of the Pep1+anti-PD-L1 antibody combination group, the Pep1 ΔC1+anti-PD-L1 antibody combination group and the Pep1ΔN2+anti-PD-L1 antibody combination group are also shown. Each peptide was administered at the dose (ng/mouse) shown in the figure.

DESCRIPTION OF EMBODIMENTS

Figure 1:
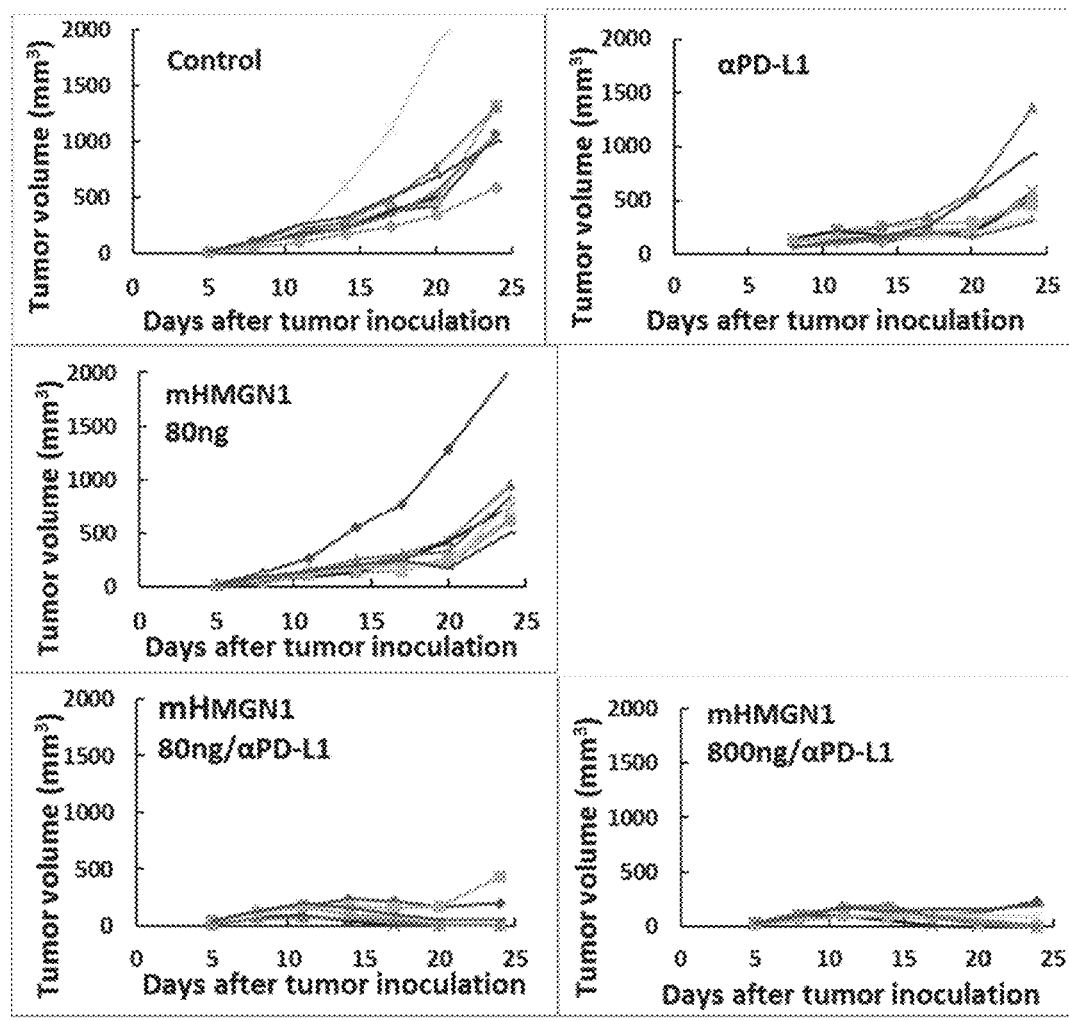
FIG. 1-1 shows time-dependent changes in tumor volume for each individual mouse in each group of Colon26 tumor-bearing mice administered with a mouse full-length HMGN1 protein (mHMGN1), and two partial peptides thereof (mPep1, mPep2) alone or in combination with an anti-PD-L1 antibody (200 μg/mouse). The HMGN1 protein and partial peptides were administered at the doses shown in the figure.

The peptide of the present invention is a peptide whose amino acid sequence is represented by any one amino acid selected from the following (1) to (9). (10) is a preferred example of (9).

(1)
(SEQ ID NO: 3)
SSAE GAAKEEPKRR SARLSAKPPA KVEAKPKKAA AKD (2) an amino acid sequence in which 1 to 8 amino acid residues at the C terminus are deleted in (1)

(3) an amino acid sequence in which 1 to 13 amino acid residues at the N terminus are deleted in (1)

(4) an amino acid sequence in which 1 to 13 amino acid residues at the N terminus are deleted in (2)

(5)
(SEQ ID NO: 12)
EGDAKGDK AKVKDEPQRR SARLSAKPA PPKPEPKPKKAPAKKGE (6)
(SEQ ID NO: 14)
GDAKGDK AKVKDEPQRR SARLSAKPA PPKPEPRPKKASAKKGE (7)
(SEQ ID NO: 15)
GQG DMRQEPKRR SARLSAMLV PVTPEVKPKRTSSSRKMKTKSD (8) an amino acid sequence in which 1 to 5 amino acid residues at the C terminus and/or 1 to 5 amino acid residues at the N terminus are deleted in any one of (5) to (7)

(9) an amino acid sequence in which 1 to 3 amino acid residues are substituted in any one of (1) to (8)

(10) an amino acid sequence in which 1 to 3 amino acid residues are substituted in any one of (1) to (4)

The peptide of the present invention may be, for example, an anti-cancer active peptide or an anti-cancer effect-enhancing peptide. The anti-cancer active peptide is a peptide having anti-cancer activity. The anti-cancer effect-enhancing peptide is a peptide having an activity of enhancing the anti-cancer effect of an anti-cancer agent. The anti-cancer activity of the anti-cancer active peptide includes activities that suppress tumor growth, metastasis, and recurrence by the peptide alone, as well as activities that additively or synergistically suppress tumor growth, metastasis, and recurrence when used in combination with other anti-cancer active ingredients. The latter activities, especially the activities that synergistically suppress tumor growth and the like, can be also understood as an anti-cancer effect-enhancing activity.

In the present invention, substitution with a conservative amino acid means exchangeability of a residue having a similar side chain, for example, in a group of amino acids having an aliphatic side chain, glycine, alanine, valine, leucine and isoleucine, in a group of amino acids with an aliphatic hydroxyl side chain, serine and threonine, in a group of amino acids with amide-containing side chains, asparagine and glutamine, in a group of amino acids with aromatic side chains, phenylalanine, tyrosine and tryptophan, in a group of amino acids with basic side chains, lysine, arginine and histidine, and in a group of amino acids with sulfur-containing side chains, cysteine and methionine. Examples of preferred substitution with a conservative amino acid include substitution between valine, leucine and isoleucine, substitution between phenylalanine and tyrosine, substitution between lysine and arginine, substitution between alanine and valine, and substitution between asparagine and glutamine.

In the present invention, an aspect of the amino acid sequence in which the C-terminal or N-terminal amino acid residue is deleted includes an amino acid sequence in which amino acid residues are continuously deleted from the C terminus or N terminus.

<Peptides Derived from Partial Regions of HMGN1 Protein>

In one embodiment, the peptide of the present invention is a peptide of the amino acid sequence (SEQ ID NO: 3) of (1), derived from a partial region of the HMGN1 protein. The amino acid sequence of SEQ ID NO: 3 is an amino acid sequence of a region of the 7th to 43rd residues of a human HMGN1 protein (GenBank Accession No. NP_004956, SEQ ID NO: 17). HMGN proteins such as NMGN1 are proteins composed of a nucleosomal binding domain (NBD), two nuclear localization signals that sandwich NBD, and a chromatin unfolding domain in the C-terminal region (Chromatin Unfolding Domain), and in human HMGN1, a region of the 14th to 42nd amino acids is NBD (Ueda et al., MOLECULAR AND CELLULAR BIOLOGY, May 2008, p. 2872-2883). SEQ ID NO: 3 is a sequence of the partial region of HMGN1 containing this NBD, and in SEQ ID NO: 3, a region of the 8th to 36th amino acids is NBD.

Also, in one embodiment, the peptide of the present invention is mPep1 (SEQ ID NO: 1).

In one embodiment, the peptide of the present invention is a peptide having an amino acid sequence of (2), derived from a partial region of the HMGN1 protein. (2) is an amino acid sequence in which 1 to 8, for example, 1 to 7, 1 to 6, 1 to 5, 1 to 4, 1 to 3, 1 to 2, or 8, 7, 6, 5, 4, 3, 2 or 1, amino acid residues at the C terminus of the amino acid sequence set forth in SEQ ID NO: 3 are deleted. Specific examples of the amino acid sequence of (2) include an amino acid sequence set forth in SEQ ID NO: 5, but the scope of the present invention is not limited to this specific example.

In one embodiment, the peptide of the present invention is a peptide having an amino acid sequence of (3), derived from a partial region of the HMGN1 protein. (3) is an amino acid sequence in which 1 to 13, for example, 1 to 12, 1 to 11, 1 to 10, 1 to 9, 1 to 8, 1 to 7, 1 to 6, 1 to 5, 1 to 4, 1 to 3, 1 to 2, or 13, 12, 11, 10, 9, 8, 7, 6, 5, 4, 3, 2 or 1, amino acid residues at the N terminus of the amino acid sequence set forth in SEQ ID NO: 3 are deleted. Specific examples of the amino acid sequence of (3) include an amino acid sequence set forth in SEQ ID NO: 7 and SEQ ID NO: 8, but the scope of the present invention is not limited to these specific example.

In one embodiment, the peptide of the present invention is a peptide having an amino acid sequence of (4), derived from a partial region of the HMGN1 protein. (4) is an amino acid sequence in which 1 to 8, for example, 1 to 7, 1 to 6, 1 to 5, 1 to 4, 1 to 3, 1 to 2, or 8, 7, 6, 5, 4, 3, 2 or 1, amino acid residues at the C terminus are deleted, and 1 to 13, for example, 1 to 12, 1 to 11, 1 to 10, 1 to 9, 1 to 8, 1 to 7, 1 to 6, 1 to 5, 1 to 4, 1 to 3, 1 to 2, or 13, 12, 11, 10, 9, 8, 7, 6, 5, 4, 3, 2 or 1, amino acid residues at the N terminus are deleted, in the amino acid sequence set forth in SEQ ID NO: 3. Specific examples of the amino acid sequence of (4) include an amino acid sequence set forth in SEQ ID NO: 18, but the scope of the present invention is not limited to this specific example.

In one embodiment, the peptide of the present invention is a peptide having an amino acid sequence of (10), derived from a partial region of the HMGN1 protein. The amino acid sequence of (10) is an amino acid sequence derived from a partial region of the HMGN1 protein among (9), and an amino acid sequence in which 1 to 3, for example, 1 or 2, or 1, amino acid residues are substituted in any one of (1) to (4). Specific examples of such an amino acid sequence include, but are not limited to, an amino acid sequence set forth in SEQ ID NO: 11 (a sequence in which one residue at the N terminus of SEQ ID NO: 3 is deleted and three R residues are substituted with D residues). An aspect of the substitution can include substitution with a conservative amino acid.

In one embodiment, the peptide of the present invention is SEQ ID NO: 3, SEQ ID NO: 5, SEQ ID NO: 7, SEQ ID NO: 8, SEQ ID NO: 11, or SEQ ID NO: 18. Alternatively, it is SEQ ID NO: 3, SEQ ID NO: 5, SEQ ID NO: 7, SEQ ID NO: 8, or SEQ ID NO: 18.

<Peptides Derived from Partial Regions Containing NBDs of HMGN2, HMGN4, and HMGN5>

In one embodiment, the peptide of the present invention is a peptide of an amino acid sequence (SEQ ID NO: 12) of (5), an amino acid sequence amino acid sequence (SEQ ID NO: 14) of (6) or an amino acid sequence (SEQ ID NO: 15) of (7), derived from a partial region containing NBD of HMGN2, HMGN4, or HMGN5. SEQ ID NOs: 12, 14 and 15 are amino acid sequences of partial regions containing NBDs of human HMGN2, human HMGN4, and human HMGN5, respectively, and are regions in each HMGN protein corresponding to regions of SEQ ID NO: 3 in human HMGN1. Regions of the 12th to 41st amino acids in SEQ ID NO: 12, the 11th to 40th amino acids in SEQ ID NO: 14, and the 6th to 35th amino acids in SEQ ID NO: 15 correspond to each NBD, respectively.

In one embodiment, the peptide of the present invention is a peptide having an amino acid sequence of (8), derived from the partial region containing NBD of HMGN2, HMGN4, or HMGN5. (8) is an amino acid sequence in which 1 to 5 amino acid residues at the C terminus, 1 to 5 amino acid residues at the N terminus, or 1 to 5 amino acid residues at the C terminus and 1 to 5 amino acid residues at the N terminus are deleted in an amino acid sequence of any one of SEQ ID NO: 12, SEQ ID NO: 14, and SEQ ID NO: 15.

In one embodiment, the peptide of the present invention is a peptide having an amino acid sequence of (9). (9) is an amino acid sequence in which 1 to 3, for example, 1 or 2, or 1, amino acid residues are substituted in any one of (1) to (8). Specific examples of such an amino acid sequence include, but are not limited to, an amino acid sequence set forth in SEQ ID NO: 11 (a sequence in which one residue at the N terminus of SEQ ID NO: 3 is deleted and three R residues are substituted with D residues). An aspect of the substitution can include substitution with a conservative amino acid. Among the peptides having the amino acid sequence of (9), the peptides having the amino acid sequence in which one to three, for example, one or two, or one, amino acid residues are substituted in any one of (5) to (8) correspond to peptides derived from the partial regions containing NBDs of HMGN2, HMGN4, and HMGN5.

The amino acid sequence of the peptide of the present invention may be any one of (1) to (7), or any one of (1) to (3) and (5) to (7) of the above. Further, the amino acid sequence of the peptide of the present invention may be any one of (1) to (4) and (10), or any one of (1) to (4) of the above. For example, the amino acid sequence of the peptide of the present invention may be any amino acid sequence selected from SEQ ID NO: 3, SEQ ID NO: 5, SEQ ID NO: 7, SEQ ID NO: 8, SEQ ID NO: 11, SEQ ID NO: 12, SEQ ID NO: 14, SEQ ID NO: 15, and SEQ ID NO: 18. In addition, the amino acid sequence of the peptide of the present invention may be, in any amino acid sequence selected from SEQ ID NO: 3, SEQ ID NO: 5, SEQ ID NO: 7, SEQ ID NO: 8, SEQ ID NO: 12, SEQ ID NO: 14, SEQ ID NO: 15, and SEQ ID NO: 18, an amino acid sequence in which 1 to 3, for example, 1 or 2, or 1, amino acid residues are substituted (preferably substituted with a conservative amino acid).

The anti-cancer agent of the present invention is a preferred example of an application example of the peptide of the present invention, and contains the peptide whose amino acid sequence is represented by any one of (1) to (9) above as an active ingredient. (10) is a preferred example of (9) as described above.

The peptide represented by the amino acid sequence (SEQ ID NO: 3) of (1) exerts an anti-tumor effect even independently as described in the examples below, and synergistically acts by a combined use with an immune checkpoint regulator such as an anti-PD-L1 antibody or an anti-CD4 antibody, and exerts a further excellent anti-tumor effect. Therefore, the peptide represented by the amino acid sequence of SEQ ID NO: 3 is useful as an active ingredient of an anti-cancer agent.

In the peptide consisting of the amino acid sequence set forth in SEQ ID NO: 3, as shown in the following examples, when 9 residues (8 residues at the C-terminal of NBD) or more at the C-terminal are removed, the synergistic anti-cancer effect is lost by the combined use with the immune checkpoint regulator, but the anti-cancer effect is maintained by removing about 5 residues (4 residues at the C-terminal of NBD). Therefore, the peptide having the amino acid sequence of (2) can also be used as an active ingredient of an anti-cancer agent, like the peptide represented by the amino acid sequence set forth in SEQ ID NO: 3.

In the peptide consisting of the amino acid sequence set forth in SEQ ID NO: 3, as shown in the following examples, when 14 residues or more at the N-terminal are removed, the synergistic anti-cancer effect is lost by the combined use with the immune checkpoint regulator, but the anti-cancer effect is maintained by removing about 8 residues. Therefore, the peptide having the amino acid sequence of (3) can also be used as an active ingredient of an anti-cancer agent, like the peptide represented by the amino acid sequence set forth in SEQ ID NO: 3.

In addition, from experimental results of the terminally deleted form of the following examples, it is understood that a region of at least the 14th to 29th residues of SEQ ID NO: 3, for example, a region of the 10th to 32nd residues (SEQ ID NO: 18) is a minimal region important for the anti-cancer effect of HMGN1 protein fragment. The amino acid sequence of (4) contains such a minimal region. Therefore, the peptide represented by the amino acid sequence of (4) can also be used as an active ingredient of an anti-cancer agent, like the peptide represented by the amino acid sequence set forth in SEQ ID NO: 3. The fact that the peptide consisting of the minimal region set forth in SEQ ID NO: 18 has an anti-cancer effect has been also specifically confirmed in the following examples.

The fact that the amino acid sequence of (5) (SEQ ID NO: 12), the amino acid sequence of (6) (SEQ ID NO: 14), and the amino acid sequence of (7) (SEQ ID NO: 15) have anti-cancer activity is as shown in the following examples. The peptides represented by these amino acid sequences can also be used as active ingredients of anti-cancer agents.

(8) is, as described above, the amino acid sequence in which 1 to 5 amino acid residues at the C terminus, 1 to 5 amino acid residues at the N terminus, or 1 to 5 amino acid residues at the C terminus and 1 to 5 amino acid residues at the N terminus are deleted in the amino acid sequence of any one of SEQ ID NO: 12, SEQ ID NO: 14, and SEQ ID NO: 15. From the results of experiments using the terminally deleted form of the human HMGN1 peptide set forth in SEQ ID NO: 3, it is considered that the peptide having such an amino acid sequence can exert an anti-tumor effect like the original peptide, so that it is useful as an active ingredient of an anti-cancer agent.

The amino acid sequence set forth in SEQ ID NO: 11 is one of the specific examples of the amino acid sequence of (9), as described above. The fact that the peptide represented by the amino acid sequence set forth in SEQ ID NO: 11 has an anti-tumor effect is as shown in the following examples.

The amino acid sequence of the peptide used as the active ingredient of the anti-cancer agent is preferably any one of (1) to (7), or any one of (1) to (4) and (10) of the above, and a particularly preferred example includes, but is not limited to, any amino acid sequence selected from SEQ ID NO: 3, SEQ ID NO: 5, SEQ ID NO: 7, SEQ ID NO: 8, SEQ ID NO: 11, SEQ ID NO: 12, SEQ ID NO: 14, SEQ ID NO: 15, and SEQ ID NO: 18.

The anti-cancer agent of the present invention may be used in combination with at least one anti-cancer active ingredient selected from an immune checkpoint regulator and an anti-CD4 antibody or antigen-binding fragment thereof. The anti-cancer agent of the present invention synergistically exerts an anti-tumor effect when used in combination with such an anti-cancer active ingredient. Hereinafter, in the present specification, for convenience of description, at least one peptide used as the active ingredient of the anti-cancer agent of the present invention may be referred to as an "active ingredient (a)", and at least one selected from an immune checkpoint regulator and an anti-CD4 antibody or antigen-binding fragment thereof may be referred to as "active ingredient (b)".

The phrase "used in combination" includes both an aspect in which a plurality of active ingredients are used as separate agents and an aspect in which a combination agent containing a plurality of active ingredients in the same preparation is used. The anti-cancer agent of the present invention is typically an agent having the former aspect, and the active ingredient (b) is generally used as an agent prepared separately from the anti-cancer agent of the present invention. The same applies when using a plurality of kinds of active ingredients (b), and an agent containing a plurality of active ingredients (b) in the same preparation may be used, but a plurality of active ingredients (b) is generally preferably each combined as separate agents. When each active ingredient is combined as a separate agent, there is an advantage that the administration site, administration timing, number of doses, dose, etc. of each active ingredient can be individually optimized. When using a plurality of kinds of anti-cancer active peptides, agents containing a plurality of anti-cancer active peptides in the same preparation may be used, or a plurality of anti-cancer active peptides each prepared as separate agents may be used, and either one can be preferably used.

The phrase "administered in combination" means that a plurality of active ingredients are administered to a patient simultaneously, sequentially, or separately. Sequential administration refers to administration of the next active ingredient immediately after the administration of one active ingredient is completed. Separate administration refers to administration of a plurality of active ingredients at intervals, for example, administration at intervals of several hours or more on the same day, or on different days during one course of treatment period. When administered simultaneously, the active ingredients formulated as separate agents may be administered at the same time, or an agent containing a plurality of ingredients in the same formulation may be administered.

One course is a small unit period including a drug administration period and a drug holiday period, as is commonly understood in the field of cancer therapy. In either case of a monotherapy or a combination dose of multiple drugs, it is general to set a drug administration period of the anti-cancer agent for one week or about several weeks and a drug holiday period for about one week as one course, and carry out the number of courses (normally several courses) determined by a doctor according to patient's condition, reduction effect of cancer, and the like.

In the present invention, the term "treatment of cancer" includes various medical treatments performed for the purpose of treating cancer in patients. Specifically, in addition to treatment of primary cancer, recurrent cancer and metastatic cancer, suppression of cancer recurrence and metastasis is also included. For example, an aspect in which the anti-cancer agent of the present invention is administered to a patient after a cancer lesion is removed by surgery for the purpose of preventing recurrence is also included in the "treatment of cancer". Therefore, the term "anti-cancer agent" includes therapeutic agents for cancers (primary cancer, recurrent cancer, metastatic cancer), cancer recurrence inhibitors, and cancer metastasis inhibitors. The term "cancer patient" includes patients who currently have cancer, as well as patients who have had cancer lesions removed by surgery.

The type of cancer targeted by the anti-cancer agent of the present invention is not particularly limited, and can be applied to various cancers including solid cancers (malignant melanomas (e.g., malignant melanoma in the skin, oral mucosa epithelial and intraorbital), non-small cell lung cancers (e.g., squamous non-small cell lung cancer and non-squamous non-small cell lung cancer), small cell lung cancers, head and neck cancers, renal cell cancers, clear cell renal cell cancers, breast cancers, ovarian cancers, serous ovarian cancers, ovarian clear cell adenocarcinomas, nasopharyngeal cancers, uterine cancers (e.g., cervical cancer, endometrial cancer and uterine corpus cancer), anal cancers (e.g., anal canal cancer), large intestine cancers, rectal cancers, colon cancers, hepatocellular carcinomas, esophageal cancers, esophageal adenocarcinomas, gastric cancers, esophagogastric junction cancers, small intestine cancers, pancreatic cancers, urothelial carcinomas (e.g., bladder cancers, upper urinary tract cancers, ureteral cancers, renal pelvic cancers and urethral cancers), prostate cancers, fallopian tube cancers, primary peritoneal cancers, pleural mesotheliomas, gallbladder cancers, bile duct cancers, biliary tract cancers, skin cancers (e.g., uveal malignant melanoma and merkel cell carcinoma), testicular cancers (germ cell tumor), vaginal cancers, vulvar cancers, penile cancers, small intestine cancers, endocrine cancers, thyroid cancers, parathyroid cancers, adrenal cancers, spinal tumors, brain tumors, glioblastoma, gliosarcomas, squamous cell carcinomas, bone and soft tissue sarcomas (e.g., Ewing sarcomas, childhood rhabdomyosarcomas and uterine leiomyosarcomas), and Kaposi sarcomas) and hematological cancers (malignant lymphoma, leukemia, multiple myeloma). For example, the anti-cancer agent of the present invention can be preferably used for solid cancer. Typical specific examples of the solid cancer include epithelial solid cancers such as lung cancer, breast cancer, stomach cancer, liver cancer, large intestine cancer, tongue cancer, thyroid cancer, kidney cancer, prostate cancer, uterine cancer, cervical cancer and ovarian cancer, and other solid cancers not classified as epithelial solid cancers such as melanoma and glioma. In one aspect, the cancer targeted by the present invention may be a cancer other than skin cancer.

In the field of peptide preparations, there have been used techniques such as adding polyethylene glycol (PEG) chains for the purpose of improving in vivo stability of peptides and increasing blood half-life (Clin Nephrol. 2006 March; 65(3): 180-90. and Proc Natl Acad Sci USA. 2005 Sep. 6; 102(36): 12962-7, etc.), mainly adding a sugar chain to the N terminus or C terminus (J Am Chem Soc. 2004 Nov. 3; 126(43): 14013-22 and Angew Chem Int Ed Engl. 2004 Mar. 12; 43(12):1516-20, etc.), making at least a part of the amino acid residue into D form (J Pharmacol Exp Ther. 2004 June; 309(3):1190-7 and J Pharmacol Exp Ther. 2004 June; 309 (3):1183-9., etc.), and appropriately modifying the Fc region of the antibody and adding (for example, J. Immunol., 154 (10), 5590-5600 (1995), Nature, 332, 563-564 (1998), Nature, 332, 738-740 (1998), BioDrugs. 2008; 22: 11-26, etc.). Such a technique may be applied to the peptide of the present invention, particularly the peptide used as the active ingredient of the anti-cancer agent.

Using SEQ ID NO: 3 as an example, "a peptide whose amino acid sequence is represented by SEQ ID NO: 3" may be a form in which other functional polypeptide like Fc region is added to a peptide consists of 37 amino acid residues arranged in the order set forth in SEQ ID NO: 3. Any functional polypeptide may be added as long as it does not lose the anti-cancer activity or the anti-cancer effect-enhancing activity of the peptide. A fusion polypeptide obtained by adding the amino acid sequence of other functional polypeptide to the amino acid sequence of SEQ ID NO: 3 contains a peptide portion consisting of the amino acid sequence of SEQ ID NO: 3. Therefore, even when the anti-cancer agent or the anti-cancer effect enhancer contains such a fusion polypeptide, the polypeptide portion that exerts anti-cancer activity or anti-cancer effect-enhancing activity (anti-cancer-active polypeptide portion or anti-cancer effect-enhancing-active polypeptide portion) is contained therein, so that it is included in "an anti-cancer agent containing the peptide represented by SEQ ID NO: 3 as an active ingredient", "an anti-cancer effect enhancer containing the peptide represented by SEQ ID NO: 3 as an active ingredient", or "an anti-cancer agent or anti-cancer effect enhancer containing the amino acid sequence of the peptide represented by SEQ ID NO: 3". Similarly, "a pharmaceutical composition containing the peptide represented by SEQ ID NO: 3 as an active ingredient" or "a pharmaceutical composition containing a peptide having the amino acid sequence represented by SEQ ID NO: 3 as an active part", and "a pharmaceutical composition containing the amino acid sequence of the peptide represented by SEQ ID NO: 3" includes pharmaceutical compositions containing the fusion polypeptide as described above.

The peptide of the present invention can be easily prepared by chemical synthesis. Specific examples of the chemical synthesis method include an Fmoc method (fluorenylmethyloxycarbonyl method), a tBoc method (t-butyloxycarbonyl method), and the like. It can also be synthesized by a conventional method using various commercially available peptide synthesizers.

Since the size of the entire polypeptide of the peptide of the present invention in the form of a fusion polypeptide to which other functional polypeptide is added is large, a gene recombination method is usually preferably used as a preparation method. Preparation of a polypeptide by a gene recombination method is a well-known conventional method. Briefly, a polynucleotide encoding the peptide of the present invention and a polynucleotide encoding a functional polypeptide are prepared, these are sequentially (in any order) incorporated into an appropriate expression vector and then introduced into a suitable host cell to express the fusion polypeptide from the expression vector in the host cell, and the fusion polypeptide may be recovered and purified from the host cell.

Among the active ingredients (b), the immune checkpoint regulator is a substance that promotes activation of immune cells by regulating a function of an immune checkpoint molecule, and includes a substance that acts inhibitorily on an inhibitory immune checkpoint molecule and a substance that acts acceleratively on a co-stimulatory immune checkpoint molecule. An aspect of the immune checkpoint regulator includes an immune checkpoint inhibitor. The term "immune checkpoint molecule" includes both receptors and ligands that function as an immune checkpoints.

The immune checkpoint is an immune escape mechanism to prevent an immune system from attacking its own body. Immune checkpoint receptors are present on T cells and interact with ligands expressed on cancer cells and antigen-presenting cells. T cells recognize antigens presented on an MHC molecule and activate them to cause an immune reaction, whereas the activation of T cells is regulated by an interaction between immune checkpoint receptor and ligand that occurs in parallel. Immune checkpoint receptors include co-stimulatory receptors and inhibitory receptors, and the T cell activation and the immune reaction are regulated by a balance between both receptors.

Cancer cells express a ligand for an inhibitory immune checkpoint receptor and utilize the receptor to escape destruction by cytotoxic T cells. Therefore, administration of an antagonist against an inhibitory receptor can interfere with a use of an immune checkpoint mechanism by cancer cells and promote killing of cancer cells by CD8$^+$ T cells. A so-called immune checkpoint inhibitor, which has been put into practical use as an anti-cancer agent in recent years, is an antibody targeting an inhibitory immune checkpoint receptor or its ligand. An anti-CTLA-4 antibody, anti-PD-1 antibody, anti-PD-L1 antibody and the like are being developed for melanoma, lung cancer, leukemia, gastric cancer, lymphoma, kidney cancer, and the like.

In addition, administration of an agonist against co-stimulatory immune checkpoint receptor can promote the immune reaction, thereby promoting the killing of cancer cells by CD8$^+$ T cells.

In the present invention, the term "antagonist" includes various substances that interfere with activation of a receptor due to a binding between the receptor and a ligand. Examples thereof include substances that bind to the receptor and interfere with the receptor-ligand binding, and substances that bind with the ligand and interfere with the receptor-ligand binding.

For example, "an antagonist against an inhibitory immune checkpoint molecule" may be an antagonistic antibody that binds to an inhibitory immune checkpoint molecule (inhibitory receptor or ligand of the receptor); a soluble polypeptide that is designed based on an inhibitory immune checkpoint ligand and does not activate the receptor; or a vector capable of expressing the polypeptide, or the like. As the inhibitory immune checkpoint molecule to be targeted, examples of the receptor include PD-1, CTLA-4, LAG-3, TIM-3, BTLA and the like, and examples of the ligand include PD-L1 (ligand for PD-1), PD-L2 (ligand for PD-1), GALS (ligand for TIM-3), HVEM (ligand for BTLA) and the like. A method for producing an antibody, and a method for producing a polypeptide by chemical synthesis or a genetic engineering technique are conventional methods well known in the art, and a person skilled in the art can prepare the antagonist against an inhibitory immune checkpoint molecule as described above by a conventional method.

"An agonist against a co-stimulatory immune checkpoint molecule" may be an antibody having agonist activity that binds to a co-stimulatory immune checkpoint receptor; a soluble polypeptide that is designed based on a co-stimulatory immune checkpoint ligand and has an effect to activate the receptor; or a vector capable of expressing the polypeptide, or the like. As the co-stimulatory immune checkpoint molecule to be targeted, examples of the receptor include CD137, OX40, GITR and the like, and examples of the ligand include CD137L (ligand for CD137), OX40L (ligand for OX40), TNFSF18 (ligand for GITR) and the like.

The immune checkpoint regulator may be an antibody against an immune checkpoint molecule (the antibody is herein referred to as "anti-immune checkpoint antibody"). Specific examples of the anti-immune checkpoint antibody include, as antagonist antibodies, anti-PD-1 antibodies, anti-CTLA-4 antibodies, anti-LAG-3-antibodies, anti-TIM-3 antibodies, anti-BTLA antibodies and the like, which bind to a receptor and inhibit binding of a ligand to the receptor, and as agonist antibodies, anti-CD137 antibodies, anti-OX40 antibodies, GITR antibodies and the like, which have an activity of binding to a receptor and activating a downstream signal pathway. Further specific examples include anti-PD-L1 antibodies, anti-PD-L2 antibodies, anti-GALS antibodies, anti-HVEM antibodies and the like, which bind to a ligand for an inhibitory immune checkpoint receptor and inhibit binding of the ligand to the receptor.

Specific examples of the immune checkpoint regulator together with known examples of known pharmaceuticals and the like include anti-CTLA-4 antibodies (e.g., Ipilimumab (YERVOY (registered trademark), Tremelimumab, AGEN-1884), anti-PD-1 antibodies (e.g., nivolumab, Cemiplimab (REGN-2810), pembrolizumab (MK-3475), Spartalizumab (PDR-001), Tislelizumab (BGB-A317), AMP-514 (MEDI0680), Dostarlimab (ANB011, TSR-042), Toripalimab (JS001), Camrelizumab (SHR-1210), Genolimzumab (CBT-501), Sintilimab (IBI308), STI-A1110, ENUM 388D4, ENUM 244C8, GLS010, MGA012, AGEN2034, CS1003, HLX10, BAT-1306, AK105, AK103, BI 754091, LZM009, CMAB819, Sym021, GB226, SSI-361, JY034, HX008, ABBV181, BCD-100, PF-06801591, CX-188, and JNJ-63723283, etc.), anti-PD-L1 antibodies (e.g., atezolizumab (RG7446, MPDL3280A), Avelumab (PF-06834635, MSB0010718C), Durvalumab (MEDI4736), BMS-936559, STI-1010, STI-1011, STI-1014, KN035, LY3300054, HLX20, SHR-1316, CS1001 (WBP3155), MSB2311, BGB-A333, KL-A167, CK-301, AK106, AK104, ZKAB001, FAZ053, CBT-502 (TQB2450), JS003 and CX-072, etc.), anti-PD-L2 antibodies (e.g., rHIgM12B7), PD-L1 fusion proteins, PD-L2 fusion proteins (e.g., AMP-224), anti-Tim-3 antibodies (e.g., MBG453), anti-LAG-3 antibodies (e.g., BMS-986016, LAG525), anti-KIR antibodies (e.g., Lirilumab), PD-1 antagonists (e.g., AUNP-12, BMS-M1 to BMS-M10 compounds, BMS-1, BMS-2, BMS-3, BMS-8, BMS-37, BMS-200, BMS-202, BMS-230, BMS-242, BMS-1001, BMS-1166, Incyte-1 to Incyte-6 compounds, CAMC-1 to CAMC-4, RG_1, and DPPA-1, etc.), PD-L1/VISTA antagonists (e.g., CA-170, etc.), PD-L1/TIM3 antagonists (e.g., CA-327, etc.), and the like. An antibody containing heavy chain and light chain complementarity determining regions (CDRs) or a variable region (VR) of the known antibodies is also an aspect of the immune checkpoint regulator. Examples of further aspect of the anti-PD-1 antibody include an antibody including heavy and light chain complementarity determining regions (CDRs) or a variable region (VR) of nivolumab.

Preferred specific examples of the immune checkpoint regulator include at least one selected from an antagonistic anti-PD-1 antibody, anti-PD-L1 antibody, anti-PD-L2 antibody, antagonistic anti-CTLA-4 antibody, agonistic anti-CD137 antibody, antagonistic anti-LAG-3 antibody, antagonistic anti-BTLA antibody and agonistic anti-GITR antibody, and particularly, at least one selected from an antagonistic anti-PD-1 antibody, anti-PD-L1 antibody, and anti-PD-L2 antibody. Particularly preferred examples of the active ingredient (b) include at least one selected from an anti-CD4 antibody having cytotoxic activity, antagonistic anti-PD-1 antibody, anti-PD-L1 antibody, and anti-PD-L2 antibody. However, the scope of the present invention is not limited to these specific examples.

Among the active ingredients (b), as the anti-CD4 antibody or antigen-binding fragment thereof, an antibody or antigen-binding fragment thereof having an action of depleting CD4-positive cells is usually used. A first example includes an anti-CD4 antibody having cytotoxic activity. A second example includes an anti-CD4 antibody or antigen-binding fragment thereof to which a cytotoxic component is bound.

The cytotoxic activity of an antibody includes antibody-dependent cytotoxic activity (ADCC activity) and complement-dependent cytotoxic activity (CDC activity). The anti-CD4 depleting antibody may have either ADCC activity or CDC activity, but one having a high cytotoxic activity capable of exerting sufficiently high killing ability to CD4$^+$ cells is used. Such an anti-CD4 antibody having a high cytotoxic activity is known to have an anti-cancer effect on various cancers (for example, WO 2015/125652 A1). The anti-CD4 depleting antibody exerts a therapeutic effect by eliminating immunodeficiency environment in solid cancer by removing CD4$^+$ cells involved in immunosuppression and promoting destruction of cancer cells by CD8$^+$ CTL (T cells). For hematological cancer, since cancer cells themselves are CD4 positive, a therapeutic effect is exerted by directly injuring the cancer cells.

In the case of ADCC activity, the term "high cytotoxic activity" refers to have a higher ADCC activity than that of known anti-CD4 antibody 6G5 (zanolimumab) and CE9.1 (keliximab) known to have ADCC activity, when the ADCC activity against CD4-expressing cells is measured using a known measurement method. Further, in the case of CDC activity, the term "high cytotoxic activity" refers to show a stronger CDC activity than that of a known anti-CD4 antibody OKT4 known to have anti-CDC activity, when the CDC activity against CD4-expressing cells in an experimental system is measured using the same complement using a known measurement method.

Methods for measuring the ADCC activity and CDC activity of an antibody are described in Cancer Immunol. Immunother, 36, 373 (1993) and the like, and are known, and commercially available kits also exist. Such a commercially available kit may be used to evaluate whether they have higher cytotoxic activity than that of known anti-CD4 antibodies. Alternatively, human peripheral blood mononuclear cells and an anti-CD4 antibody were mixed and reacted at 37° C. for several hours, the ratio of CD3$^+$ cells to CD8$^+$ cells in a reaction solution was measured by flow cytometric analysis, and the obtained measured value was compared with a measured value when using the anti-CD4 antibody having no ADCC activity or the above-mentioned known anti-CD4 antibody, whereby it is possible to evaluate the strength of the ADCC activity of the anti-CD4 antibody.

Preferably, an anti-CD4 antibody having a high cytotoxic activity has an ADCC activity that is 10 times or more, more preferably 100 times or more higher than those of the known anti-CD4 antibodies 6G5 and CE9.1, or has a CDC activity that is 10 times or more, more preferably 100 times or more higher than that of the known anti-CD4 antibody OKT4. As used herein, the term "10 times or more" means, for example, that the minimum antibody concentration at which a given antibody exerts a cytotoxic activity against a certain amount of cells is one-tenth or less of that of the above-described known antibody. As for an affinity of the anti-CD4 antibody to CD4, the antibody binding activity $K_D$ may be about $1 \times 10^{-9}$M or less.

An anti-CD4 antibody having a high cytotoxic activity can be created, for example, from a monoclonal anti-CD4 antibody created by a known method or from an already established known anti-CD4 antibody, by increasing the cytotoxic activity of the antibody by a method known in the art. In addition, an anti-CD4 antibody that specifically recognizes CD4 expressed on the cell surface and has a strong cytotoxic activity is also publicly known. For example, WO 2010/074266 A1 discloses an anti-CD4 antibody with more enhanced ADCC activity than conventional anti-CD4 antibodies. A humanized anti-CD4 antibody IT1208 having ADCC activity enhanced by POTELLIGENT technology set forth below is also known. Such known anti-CD4 depleting antibody can also be preferably used.

A method per se for preparing a monoclonal antibody is a conventional method well known in the art. For example, when prepared by a well-known hybridoma method, an animal (except human) is immunized with a CD4 protein or appropriate fragment thereof (extracellular region, e.g., a region from the N terminus to the 394th of CD4), antibody-producing cells such as spleen cells or lymphocytes from the animal are collected, the antibody-producing cells are fused with myeloma cells to prepare hybridomas, a hybridoma which produces an antibody that binds to the CD4 protein is screened, the hybridoma is grown, and an anti-CD4 monoclonal antibody can be obtained from a culture supernatant. The gene sequence, amino acid sequence, three-dimensional structure, and the like of CD4 have been deposited in public databases, for example, under the accession number of M12807 in GenBank of NCBI. The CD4 protein or appropriate fragment thereof to be used as an immunogen can be easily prepared by a well-known genetic engineering technique based on such sequence information.

When administered to a human, the anti-CD4 depleting antibody is desirably a human chimeric antibody against human CD4, a humanized antibody (prepared by transplanting a CDR region of a non-human-derived antibody into the corresponding region of a human antibody), or a recombinant human antibody (the same antibody as an antibody produced in the body of human, which is produced using a non-human animal or a human cell line). Methods for preparing a human chimeric antibody, a humanized antibody and a recombinant human antibody have also been established as methods well known in the art. For example, an anti-CD4 human antibody can be prepared by using CDR sequence fragments that ensure CD4 recognition prepared by cassette modification method.

Methods for increasing the cytotoxic activity of an antibody are also known, and any of these methods may be used. An example of the known methods will be described below.

One of the methods for enhancing the ADCC activity is the POTELLIGENT (registered trademark) technology for removing fucose (core fucose) contained in sugar chains present in a Fc portion of an antibody (Yamane-Ohnuki N, Satoh M, Production of therapeutic antibodies with controlled fucosylation, MAbs 2009; 1: 230-236.). The enzyme that adds core fucose is encoded by a gene named FucT-8 (Fut-8), so that an antibody molecule with enhanced ADCC activity can be obtained by expressing a gene encoding a recombinant antibody in Fut-8 knockout animal cells (Yamane-Ohnuki N, et al., Establishment of FUT8 knockout Chinese hamster ovary cells:an ideal host cell line for producing completely defucosylated antibodies with enhanced antibody-dependent cellular cytotoxicity, Biotechnol Bioeng 2004; 87:614-622.).

Another method for enhancing the ADCC activity is a method of converting sugar chains present in the Fc site of the antibody. In this method, addition of core fucose is avoided by introducing GlcNAc in an antenna-type branched sugar chain region by GnT-III gene manipulation (M. Schuster et al., Improved effector functions of a therapeutic monoclonal Lewis Y-specific antibody by glycoform engineering, Cancer Res 2005; 65:7934-7941.). An anti-CD4 antibody with enhanced ADCC activity created by such a method may be used.

A known example of a method for enhancing the CDC activity is COMPLEGENT (registered trademark) technology in which a part of isotype IgG1 is combined with a sequence of isotype IgG3 to enhance the CDC activity (Natsume A, In M, Takamura H, et al. Engineered antibodies of IgG1/IgG3 mixed isotype with enhanced cytotoxic activities, Cancer Res. 2008; 68:3863-3872.).

Another known example is AccretaMab (registered trademark) technology in which the cytotoxic activity of an antibody is strongly increased by combining the POTELLIGENT (registered trademark) technology and COMPLEGENT (registered trademark) technology described above (Natsume A, et al., Improving effector functions of antibodies for cancer treatment:Enhancing ADCC and CDC, Drug Des Devel Ther. 2009; 3:7-16). An anti-CD4 antibody having both ADCC activity and CDC activity enhanced by such a technique may be used.

When an anti-CD4 antibody or antigen-binding fragment thereof to which a cytotoxic component is bound is used as the active ingredient (b), CD4 positive cells are damaged by the cytotoxic component, and thus a cytotoxic activity as an effector function of the antibody is not necessary. The cytotoxic component refers to a substance having an activity to destroy living cells, and includes biological toxic substances, chemical substances, radioactive substances, and the like.

The antigen-binding fragment may be any antibody fragment as long as it retains the binding capacity (antigen-antibody reactivity) to the corresponding antigen of its original antibody. Specific examples include, but are not limited to, Fab, F(ab')$_2$, scFv, and the like. Fab and F(ab')$_2$ can be obtained, as is well known, by treatment of a monoclonal antibody with a protease such as papain or pepsin. Methods for preparing scFv (single chain fragment of variable region, single chain antibody) are also well known. For example, scFv can be obtained by extracting mRNA from a hybridoma prepared as described above, preparing single-stranded cDNA, performing PCR using primers specific to immunoglobulin H chain and L chain to amplify immunoglobulin H-chain gene and L-chain gene, linking these using a linker, giving an appropriate restriction enzyme site(s) to the resulting product, introducing the product into a plasmid vector, transforming E. coli with the resulting vector to allow expression of scFv, and then recovering the expressed scFv from E. coli.

A subject to which the active ingredient (a), or a combination of the active ingredients (a) and (b) is administered is a cancer patient, that is, a patient in need of treatment of cancer, and a patient who actually has cancer, and a patient after a cancer lesion is removed by surgery are included. The patient is typically, but not limited to, a mammal, especially a human. The definition of the term "treatment of cancer" is as described above.

The peptide of the present invention may be administered at any dose as long as it is effective for treating cancer. The effective amount can be appropriately selected according to tumor size, symptoms, age and body weight of the patient, and the like. The dose of the anti-cancer agent of the present invention may be, but not limited to, about 1 ng to 1 mg, e.g., about 100 ng to 100 µg, per 1 kg body weight, in terms of the effective amount per day for a subject (the effective amount per day as used herein refers to, when the active ingredient peptide is a form in which other functional polypeptide such as Fc region is added, the amount of a peptide portion consisting of the amino acid sequences of (1) to (9), and when a plurality of peptides are administered, the total amount thereof). The daily dose may be administered once, or dividedly in several times. Further, the anti-cancer agent during the treatment period with the anti-cancer agent of the present invention may be administered once, or daily for several days, or multiple times every several days, weeks or months.

The administration route of the anti-cancer agent of the present invention may be oral administration or parenteral administration, but generally, parenteral administration such as intramuscular administration, subcutaneous administration, intravenous administration or intraarterial administration is preferred. Systemic or local administration may be used. In the case of local administration, it can be administered, for example, into or near the tumor tissue or to regional lymph nodes near the tumor. The term "systemic administration" means administration to a site different from the tumor tissue, near the tumor tissue and the regional lymph nodes near the tumor, and systemic administration includes oral administration, intravenous and intraarterial administration, as well as subcutaneous and intramuscular administration.

When the peptide of the present invention is used in combination with an immune checkpoint regulator, the dose of the immune checkpoint regulator is also appropriately selected according to tumor size, symptoms, age and body weight of the patient, and the like. It may be used in the same dose, administration route, and administration schedule as in the case of using a known immune checkpoint regulator for treating cancer, and it is generally administered multiple times daily or every several days during the treatment period. However, since a high anti-cancer effect can be obtained by using it in combination with the active ingredient (a), it is also possible to reduce the dose and the number of doses as compared with the case where a known immune checkpoint regulator is usually used. It may be administered on the same schedule as the HMG protein or a recombinant vector capable of expressing the protein, or administered on a different schedule. The administration route may be oral administration or parenteral administration, but generally, parenteral administration such as intramuscular administration, subcutaneous administration, intravenous administration or intraarterial administration is preferred. Systemic or local administration may be used, but systemic administration is preferred.

When the peptide of the present invention is used in combination with an anti-CD4 antibody, the dose of the anti-CD4 antibody is also appropriately selected according to tumor size, symptoms, age and body weight of the patient, and the like. The dose thereof may be, but not limited to, about 0.001 mg/kg to 1000 mg/kg, e.g., about 0.01 mg/kg to 100 mg/kg, per 1 kg body weight, in terms of the effective amount per day for a subject. The daily dose may be administered once, or dividedly in several times. The anti-CD4 antibody during the treatment period may be administered once, or daily for several days, or multiple times every several days, weeks or months. It may be administered on the same schedule as the HMG protein or a recombinant vector capable of expressing the protein, or administered on a different schedule. The administration route of the anti-CD4 antibody may be oral administration or parenteral administration, but generally, parenteral administration such as intramuscular administration, subcutaneous administration, intravenous administration or intraarterial administration is preferred. Systemic or local administration may be used, but systemic administration is preferred. The same applies to administration of an anti-CD4 antibody or antigen-binding fragment thereof to which a cytotoxic component is bound.

When the active ingredients (a) and (b) are used in combination, as described above, the active ingredients (a) and (b) may be administered simultaneously, or may be administered sequentially or separately. When administered sequentially or separately, either may be administered first. In the following examples, administration of the active ingredient (b) is started first, but the present invention is not limited to this, and administration of the active ingredient (a) may be started first.

Each active ingredient can be formulated by appropriately mixing with additives such as pharmaceutically acceptable carriers, diluents, excipients, binders, lubricants, disintegrants, sweetening agents, suspending agents, emulsifying agents, coloring agents, flavoring agents and stabilizers, suitable for each administration route. Examples of the dosage form include oral agents such as tablets, capsules, granules, powders and syrups, and parenteral agents such as inhalants, injections, suppositories, and liquids. Formulation methods and additives which can be used are well known in the field of pharmaceutical formulation, and any of the methods and additives can be used.

The pharmaceutical composition of the present invention includes at least one peptide of the present invention, and at least one additive selected from pharmaceutically acceptable carriers, diluents, excipients, binders, lubricants, disintegrants, sweetening agents, suspending agents, emulsifying agents, coloring agents, flavoring agents, stabilizers and the like.

The anti-cancer agent of the present invention exerts an excellent anti-tumor effect, especially by the combined use with the active ingredient (b) such as an immune checkpoint regulator. This combined effect can also be understood as an activity of enhancing the anti-cancer effect of the anti-cancer agent combined with the peptide of the present invention. The anti-cancer effect enhancer for an anti-cancer agent containing the above-mentioned peptide of the present invention as an active ingredient is an invention expressing the anti-cancer activity of the peptide from such a viewpoint. An example of the anti-cancer agent is an anti-cancer agent containing the above-mentioned active ingredient (b) as an active ingredient. Preferred examples of the peptides used as the active ingredient of the anti-cancer effect enhancer, preferred examples of the active ingredient (b), and preferred examples of the dose and administration method are the same as these preferred examples of the anti-cancer agent of the present invention.

EXAMPLES

Hereinafter, the present invention will be described more specifically based on examples. However, the present invention is not limited to the following examples.

<Materials>

Tumor-Bearing Mouse:

Seven-week-old male BALB/c mice were used in groups of 8 mice, and Colon26 large intestine cancer cells were subcutaneously transplanted into the right flank at $2\times10^5$ cells/mouse.

Antibody:

An anti-mouse PD-L1 antibody (clone 10F.9G2) and an anti-mouse CD4 depleting antibody (clone GK1.5) were purchased from BioXcell.

HMGN Peptides, HMGN1 Protein:

The amino acid sequences of the HMGN peptides used in this experiment are shown in Table 1 below. Peptides were prepared by conventional chemical synthesis. As the mouse full-length HMGN1 protein (SEQ ID NO: 16), a recombinant protein was purchased from CUSABIO TECHNOLOGY LLC.

TABLE 1

| | | |
|---|---|---|
| mouse HMGN1 NBD-peptide 1 (mPep1) | SADG AAKAEPKRRS ARLSAKPAPA KVDAKPKKAA GKD 37aa, pI: 10.45, MW: 3744.32 | SEQ ID NO: 1 |
| mouse HMGN1 NBD-peptide 2 (mPep2) | V QIKGKRGAKG KQADVADQQT TELPAENGET ENQSPASEE 40aa, pI: 4.60, MW: 4240.52 | SEQ ID NO: 2 |
| Human HMGN1 NBD-peptide 1 (Pep1) | SSAE GAAKEEPKRR SARLSAKPPA KVEAKPKKAA AKD 37aa, pI: 10.21, MW: 3860.43 | SEQ ID NO: 3 |
| Human HMGN1 NBD-peptide 1 Δ C (Pep1 Δ C) | SSAE GAAKEEPKRR SARLSAKPPA 24aa; pI: 10.27, MW: 2494.79 | SEQ ID NO: 4 |
| Human HMGN1 NBD-peptide 1 Δ C1 (Pep1 Δ C1) | SSAE GAAKEEPKRR SARLSAKPPA KVEAKPKK 32aa, pI: 30.38, MW: 3403.93 | SEQ ID NO: 5 |
| Human HMGN1 NBD-peptide 1 Δ C2 (Pep1 Δ C2) | SSAE GAAKEEPKRR SARLSAKPPA KVEA 28aa, pI: 9.99, MW: 2922.29 | SEQ ID NO: 6 |

TABLE 1-continued

| | | |
|---|---|---|
| Human HMGN1 NBD-peptide 1 Δ N1 (Pep1 Δ N1) | AAKEEPKRR SARLSAKPPA KVEAKPKKAA AKD 32aa, pI: 10.45, MW: 3429.03 | SEQ ID NO: 7 |
| Human HMGN1 NBD-peptide 1 Δ N2 (Pep1 Δ N2) | EPKRR SARLSAKPPA KVEAKPKKAA AKD 28aa, pI: 10.71, MW: 3029.58 | SEQ ID NO: 8 |
| Human HMGN1 NBD-peptide 1 Δ N3 (Pep1 Δ N3) | SARLSAKPPA KVEAKPKKAA AKD 23aa, pI: 10.29, MW: 2362.80 | SEQ ID NO: 9 |
| Human HMGN1 NBD-peptide 1 core (Pep1 core) | IPKRR SARLSAKPPA KVEAKPKK 23aa, pI: 11.17, MW: 2573.08 | SEQ ID NO: 18 |
| Human HMGN1 peptide O (PepO) | KEEPKRR SARLSAKPPA KVEAKPKKAA AKDKSSDKK 36aa, pI: 10.41, MW: 3960.64 | SEQ ID NO: 10 |
| Human HMGN1 NBD-peptide 1 mutant (Pep1 mutant) | SAE GAAKEEPKDD SADLSAKPPA KVEAKPKKAA AKD 36aa, pI: 6.09, MW: 3650.06 | SEQ ID NO: 11 |
| Human HMGN2 NBD-peptide (N2Pep) | EGDA KGDK AKVKDEPQRR SARLSAKPA PPKPEPKPKKAPAKKGE 44aa, pI: 10.07, MW: 4718.44 | SEQ ID NO: 12 |
| Human HMGN3 NBD-peptide (N3Pep) | SPENTEG KDGS KVTKQEPTRR SARLSAKPA PPKPEPTPRKTSAKKE 46aa, pI: 10.28, MW: 5026.69 | SEQ ID NO: 13 |
| Human HMGN4 NBD-peptide (N4Pep) | GDA KGDK AKVKDEPQRR SARLSAKPA PPKPEPRPKKASAKKGE 43aa, pI: 10.35, MW: 4607.30 | SEQ ID NO: 14 |
| Human HMGN4 NBD-peptide (N5Pep) | GQG DMRQEPKRR SARLSAMLV PVTPEVKPKRTSSSRKMKTKSD 43aa, pI: 11.41, MW: 4856.66 | SEQ ID NO: 15 |

<Method and Result>

The HMGN peptide was intraperitoneally administered at a dose described below four times in total at 9, 14, 17 and 20 days after tumor cell implantation. The anti-mouse PD-L1 antibody was intraperitoneally administered at 200 μg/mouse four times in total at 4, 8, 14 and 18 days after tumor cell implantation. The anti-mouse CD4 antibody was intraperitoneally administered at a dose of 200 μg/mouse twice in total at 5 and 9 days after tumor cell implantation. The long diameter and short diameter of the solid tumor were measured every 3 to 4 days, and tumor volume was calculated by the following calculation formula.

Tumor volume $(mm^3)$=(Long diameter; mm)×(Short diameter; mm)$^2$×0.5236

1. Synergistic Anti-Tumor Effect by Combined Use of Mouse HMGN1 NBD Peptide 1 and Anti-PD-L1 Antibody FIG. 1 shows time-dependent changes in tumor volume for each individual mouse when a mouse full-length HMGN1 protein (HMGN1, SEQ ID NO: 16, administered at 80 or 800 ng/mouse four times in total), mouse HMGN1 NBD peptide 1 (mPep1, SEQ ID NO: 1, administered at 30 or 300 ng/mouse four times in total), and mouse HMGN1 NBD peptide 2 (mPep2, SEQ ID NO: 2, administered at 33 or 330 ng/mouse four times in total) consisting of a region at the C-terminal side of mouse HMGN1 NBD are used alone or in combination with an anti-PD-L1 antibody. When used in combination with the anti-PD-L1 antibody, mPep1 synergistically suppressed tumor growth, and at doses of 30 ng and 300 ng, Colon26 solid tumors completely regressed in 5 to 7 out of 8 mice. On the other hand, mPep2 showed no combined effect.

Figures 1, 2:
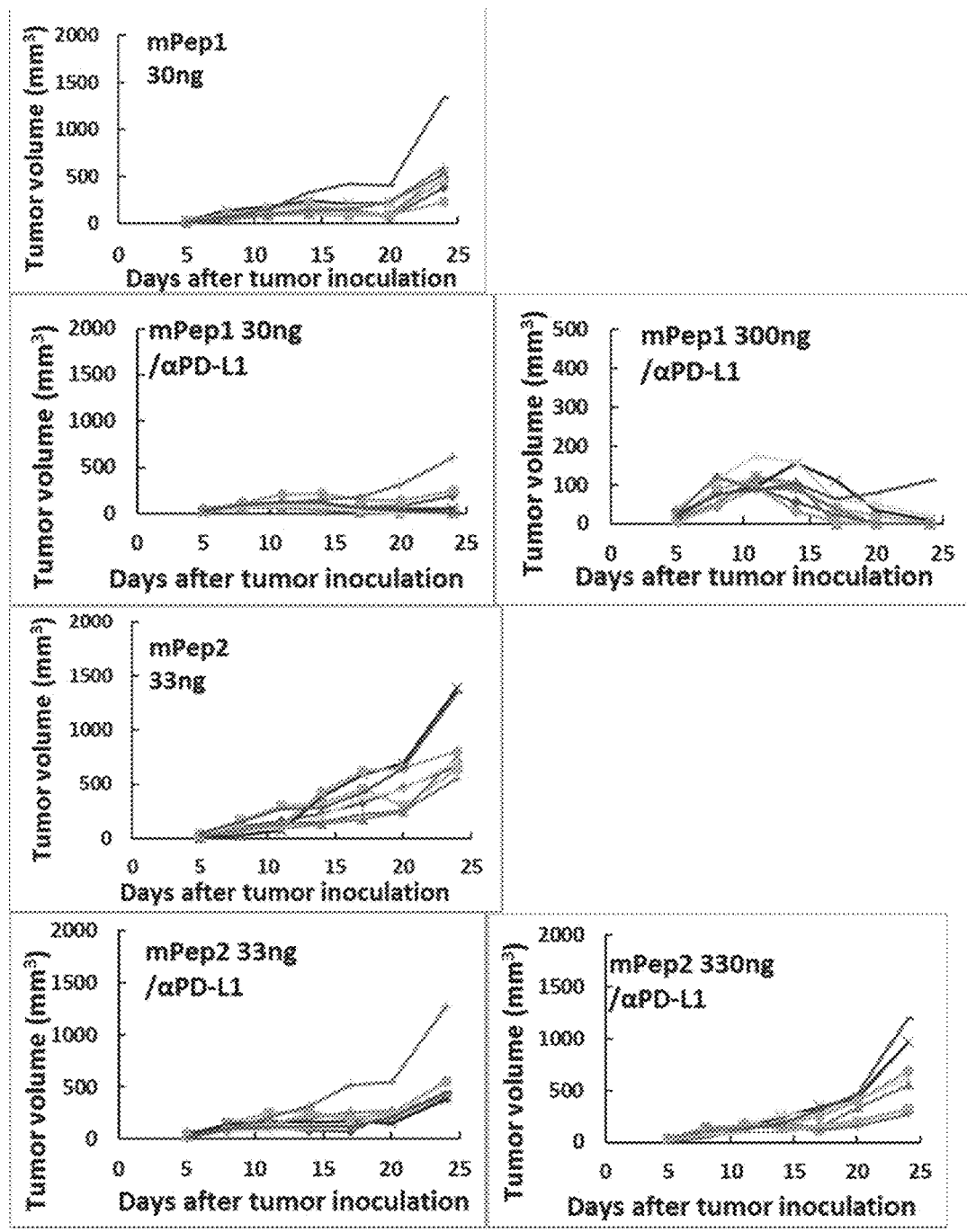
Figure 2:
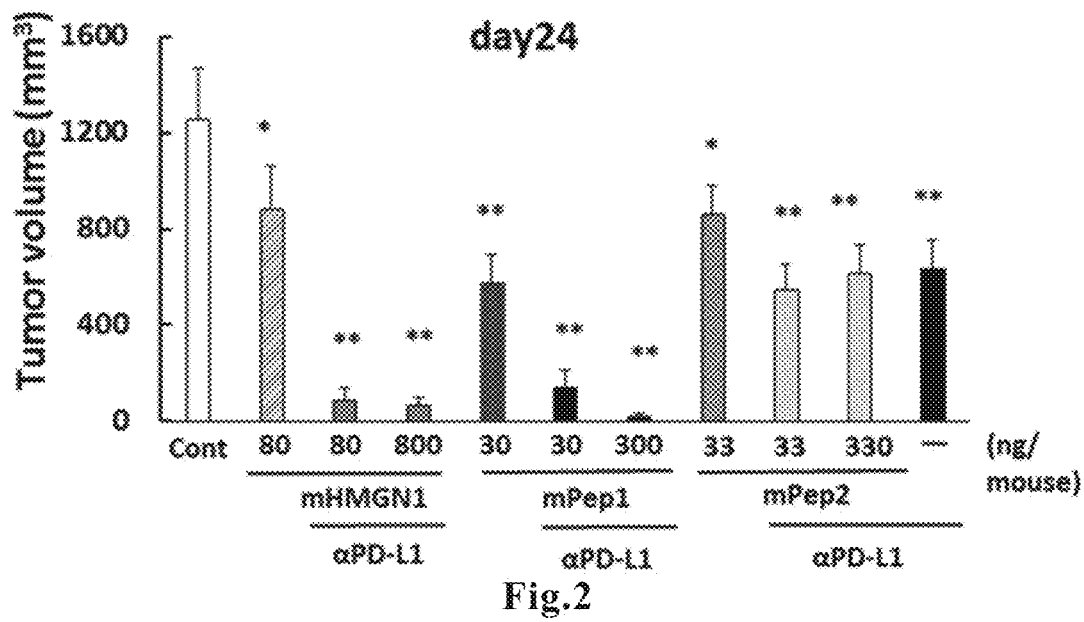

FIG. 2 shows a result of comparing the measurement results of tumor volume 24 days after Colon26 tumor cell implantation between the administration groups. mPep1 and mPep2 were administered at the same molar number. mPep1 showed a synergistic effect with the anti-PD-L1 antibody at doses of 30, 300 ng/mouse (significant difference from the control group is *: $p<0.05$, **: $p<0.01$ (Dunnett)), and complete regression of solid tumors was observed at day 24 in 4 of out of 8 mice. On the other hand, mPep2 was ineffective.

When the full-length protein and its fragment are compared, the full-length protein usually has a longer half-life in blood. However, the results of this experiment showed that mPep1 showed an equal or higher anti-tumor effect at a dose lower than that of the mouse full-length HMGN1 protein, suggesting that the half-life of mPep1 is similar to that of the full-length HMGN1 protein.

2. Anti-Tumor Effect of Human HMGN1 NBD Peptide 1

A partial fragment (human HMGN1 NBD peptide 1; Pep1, SEQ ID NO: 3) of human HMGN1 (SEQ ID NO: 17) corresponding to mPep1 was prepared and administered to Colon26 tumor-bearing mice alone or in combination with an anti-PD-L1 antibody (200 μg/mouse), and the anti-tumor effect was investigated.

Figure 3:
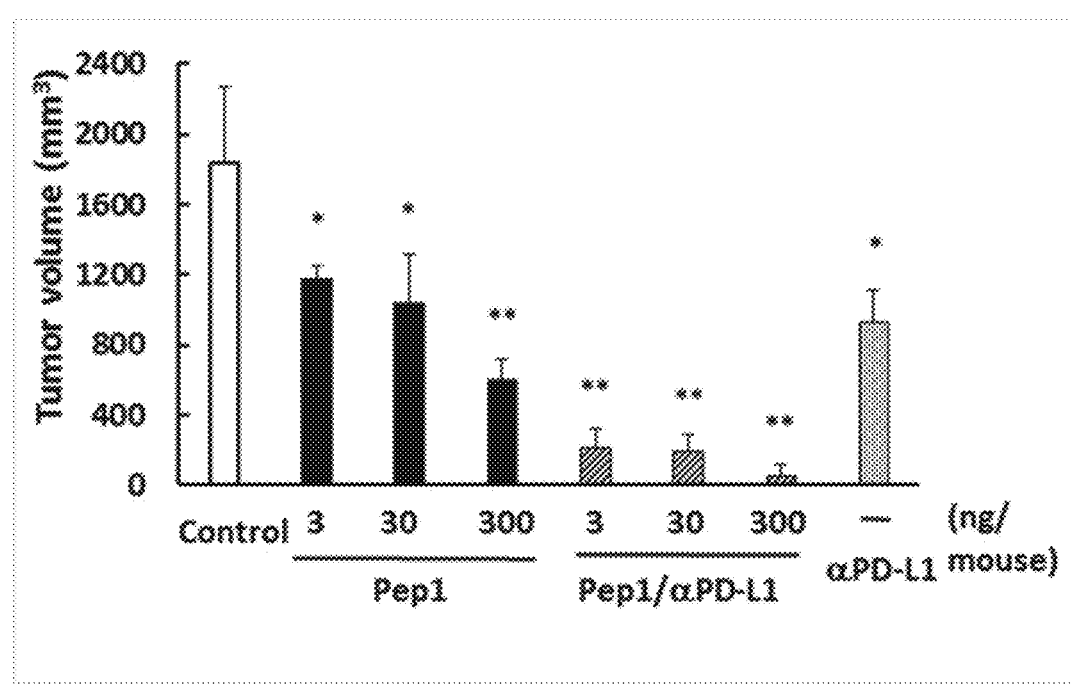
FIG. 3 shows measurement results of tumor volume 24 days after tumor cell implantation in each group of Colon26 tumor-bearing mice administered with a human HMGN1 partial peptide (Pep1) alone or in combination with an anti-PD-L1 antibody (200 μg/mouse). Pep1 was administered at the dose shown in the figure. Significant difference from the control group *: $p<0.05$, **: $p<0.01$ (Dunnett).
Figures 1, 4:
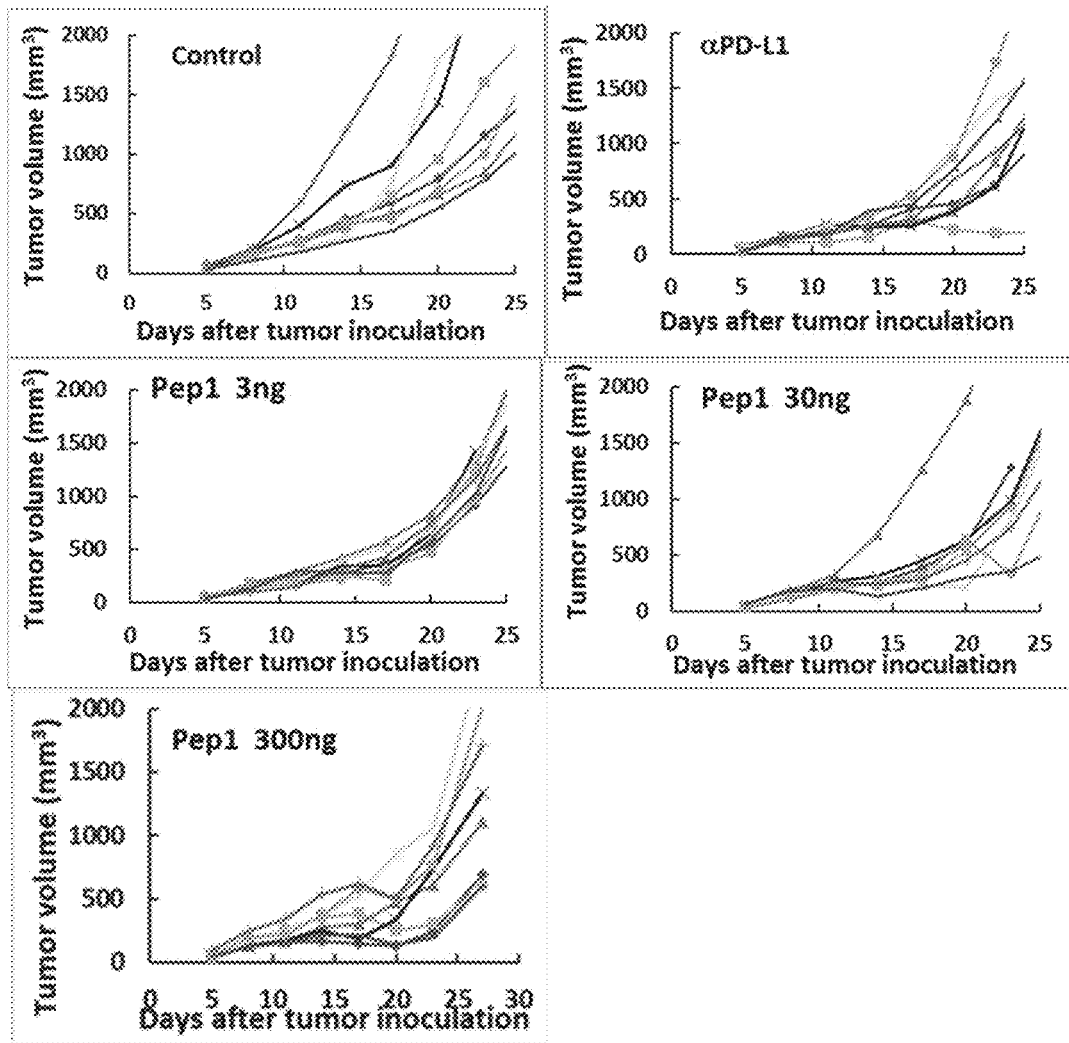
Figures 2, 4:
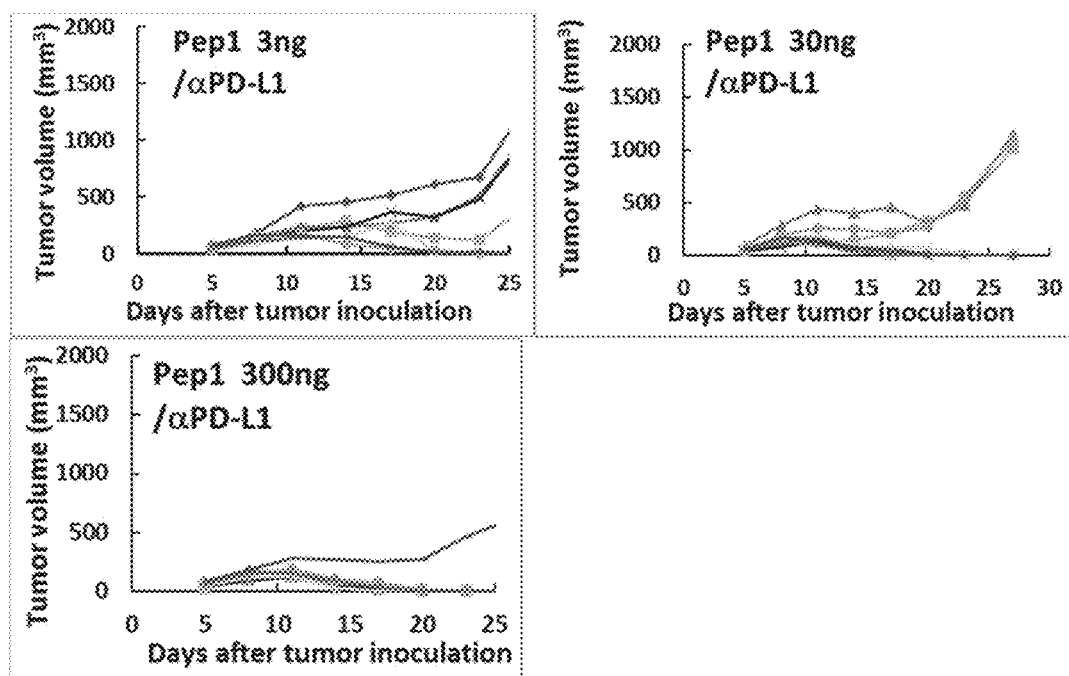

FIG. 3 shows a result of measuring tumor volume 23 days after tumor implantation and comparing between the control group (Colon26 tumor-bearing mice group to which neither peptide nor anti-PD-L1 antibody was administered) and the administration groups. FIG. 4 shows time-dependent changes in tumor volume for each individual mouse in a Pep1 single administration group and a Pep1+anti-PD-L1 antibody combination group. Pep1, even independently, significantly suppressed growth of Colon26 solid tumor in a dose-dependent manner (FIG. 3, significant difference from the control group *: p<0.05, **: p<0.01 (Dunnett)). When used in combination with the anti-PD-L1 antibody, Pep1 synergistically suppressed tumor growth, and at doses of 30, 300 ng, Colon26 solid tumors completely regressed in 5 to 7 of 8 mice. In addition, since the human sequence peptides were also effective in mice, it was suggested that there is no species difference in the anti-tumor effects of the HMGN peptides.

3. Search for Regions Important for Anti-Tumor Effect of HMGN1 NBD Peptide 1

As C-terminal deletion peptides of Pep1, Pep1ΔC (SEQ ID NO: 4) in which C-terminal 13 residues of Pep1 were removed, Pep1ΔC1 (SEQ ID NO: 5) in which C-terminal 5 residues of Pep1 were removed, and Pep1ΔC2 (SEQ ID NO: 6) in which C-terminal 9 residues of Pep1 were removed were prepared. Further, as N-terminal deletion peptides of Pep1, Pep1ΔN1 (SEQ ID NO: 7) in which N-terminal 5 residues of Pep1 were removed, Pep1ΔN2 (SEQ ID NO: 8) in which N-terminal 9 residues of Pep1 were removed, and Pep1ΔN3 (SEQ ID NO: 9) in which N-terminal 14 residues of Pep1 were removed were prepared. Furthermore, a Pep1 mutant (SEQ ID NO: 11) having a sequence in which N-terminal 1 residue of Pep1 was removed, and three R residues were replaced by D residues was prepared. These peptides were administered to Colon26 tumor-bearing mice each in combination with an anti-PD-L1 antibody (200 µg/mouse), and tumor volume was measured over time. As the peptide dose, using a Pep1 dose of 300 ng/mouse as a reference, the same number of moles was intraperitoneally administered. For the peptides (Pep1ΔN1, Pep1ΔN2, Pep1 mutant) administered in two doses, the common ratio was set to 5, and the same number of moles was similarly administered.

Figures 1, 5:
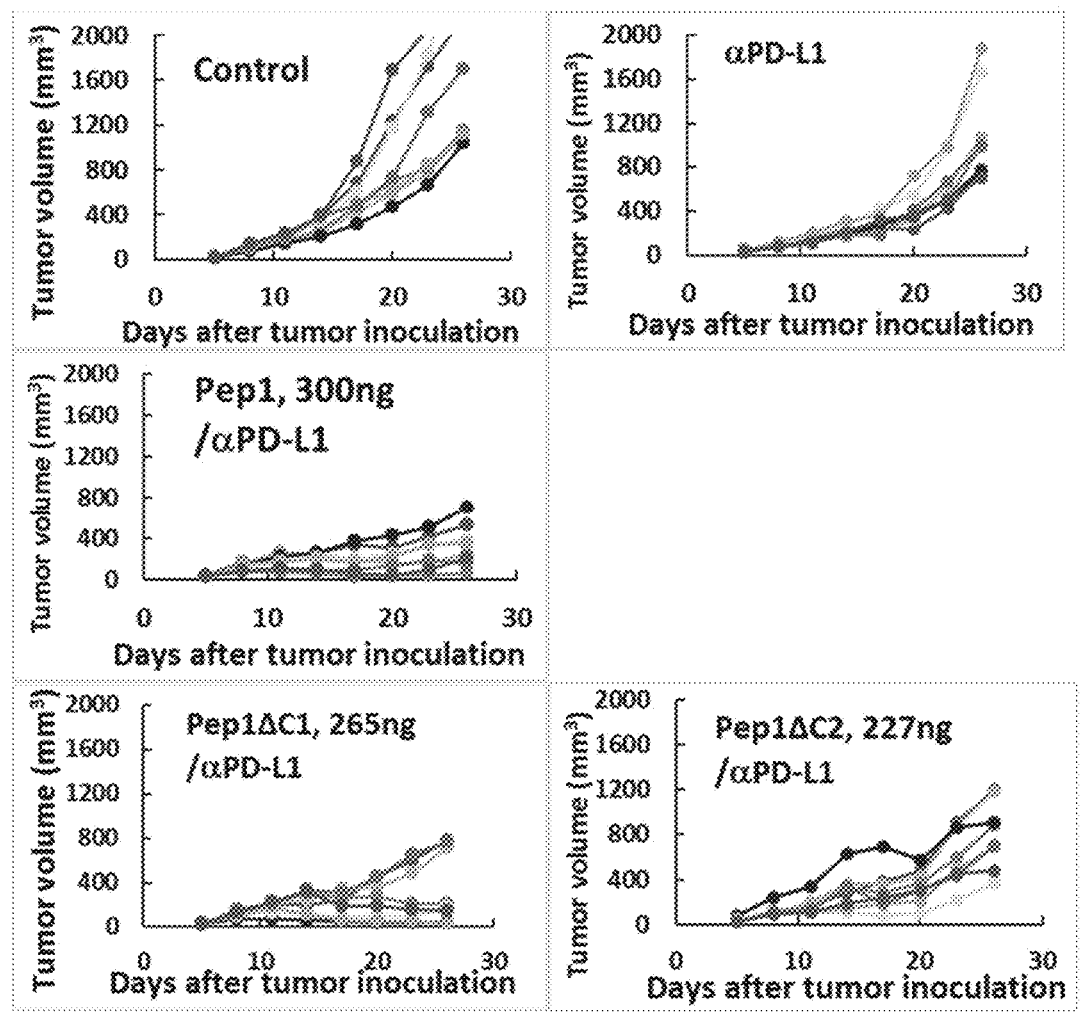
Figures 2, 5:
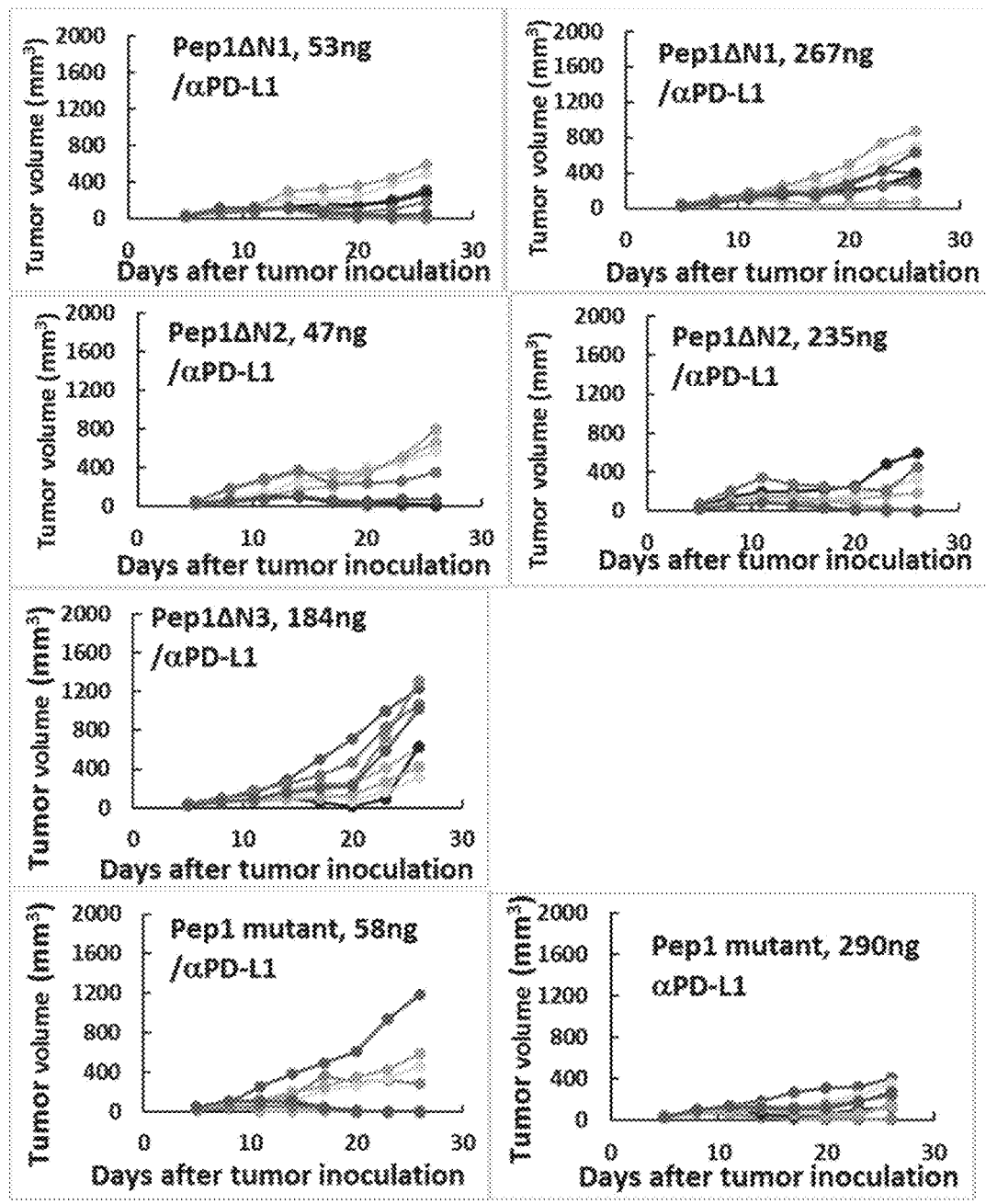
Figure 6:
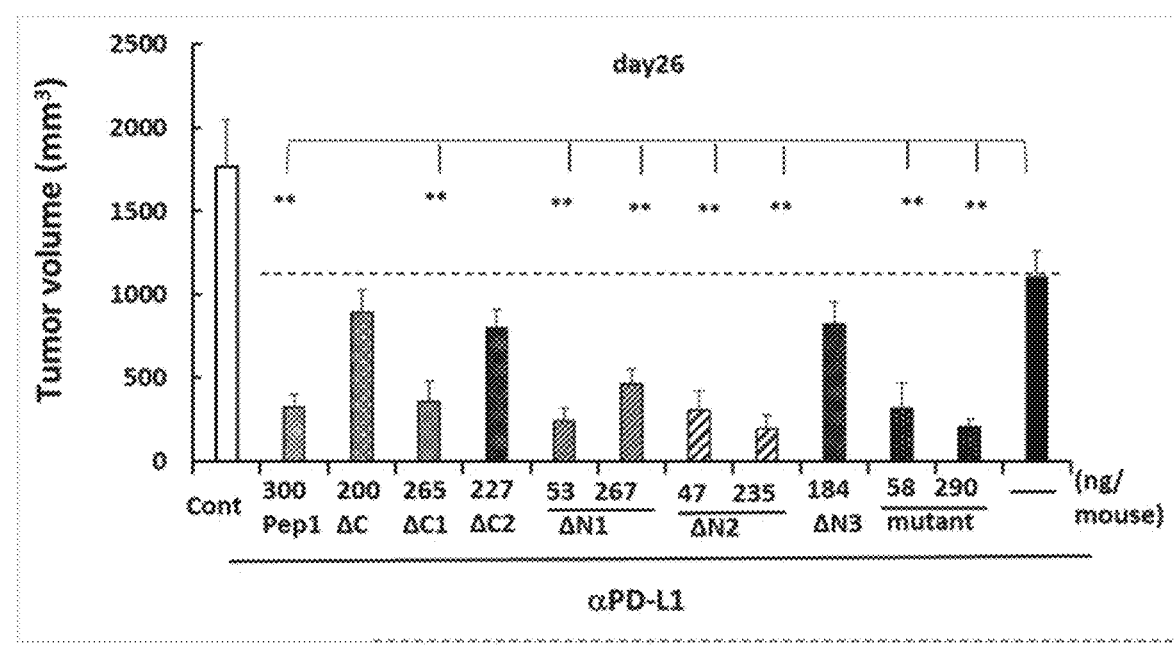
FIG. 6 shows measurement results of tumor volume 26 days after tumor cell implantation in each group of Colon26 tumor-bearing mice administered with various terminally deleted forms and R→D substitutions of Pep1, each in combination with an anti-PD-L1 antibody (200 μg/mouse). Each peptide was administered at the dose shown in the figure. Significant difference from the anti-PD-L1 antibody single administration group **: $p<0.01$ (Dunnett).

FIG. 5 shows time-dependent changes in tumor volume for each individual mouse. FIG. 6 shows a result of comparing tumor volumes 26 days after tumor cell implantation between the administration groups (significant difference from the anti-PD-L1 antibody single administration group **: p<0.01 (Dunnett)). In the Pep1+anti-PD-L1 antibody combination group, as also shown in FIGS. 3 and 4, the growth of Colon26 solid tumor was significantly suppressed. Even in the Pep1ΔC1+anti-PD-L1 antibody combination group, the growth of Colon26 solid tumor was significantly suppressed. On the other hand, in the combination group of Pep1ΔC2 in which 4 more C-terminal amino acid residues were further removed from Pep1 ΔC1 and anti-PD-L1 antibody, even a dose equimolar to other peptides was ineffective, and the anti-tumor effect of the peptide was lost. It was confirmed that the anti-tumor effect of the peptide was lost even in Pep1 ΔC in which C-terminal residues were further removed from Pep1ΔC2.

Pep1ΔN1 significantly suppressed Colon26 solid tumor growth at doses of 53 and 267 ng/mouse. Pep1ΔN2 similarly suppressed solid tumors, and solid tumors completely regressed in 2 to 4 mice. On the other hand, in the combination group of Pep1ΔN3 in which 5 more N-terminal amino acid residues were further removed from Pep1ΔN2 and anti-PD-L1 antibody, even a dose equimolar to other peptides was ineffective, and the anti-tumor effect of the peptide was lost.

Based on the above results that the anti-tumor effects of the peptides were maintained in Pep1ΔC1 and Pep1ΔN2 and the anti-tumor effects of the peptides were lost in Pep1ΔC2 and Pep1ΔN3, it was assumed that a region of the 10th to 32nd residues of Pep1 retained in Pep1ΔC1 and Pep1ΔN2 was the smallest activity unit (core) as an anti-tumor peptide. Therefore, a peptide consisting of the region was prepared as Peptide1 core (Pep1core), and the anti-tumor effect was compared with Pep1, Pep1ΔC1 and Pep1ΔN2. As the peptide dose, using Pep1 doses of 300 ng and 60 ng/mouse as references, the same number of moles was intraperitoneally (i.p.) administered. Further, for the peptides (Pep1core, Pep1ΔC1, Pep1ΔN2) administered in three doses, the common ratio was set to 5, and the same number of moles was similarly intraperitoneally administered.

Figures 1, 7:
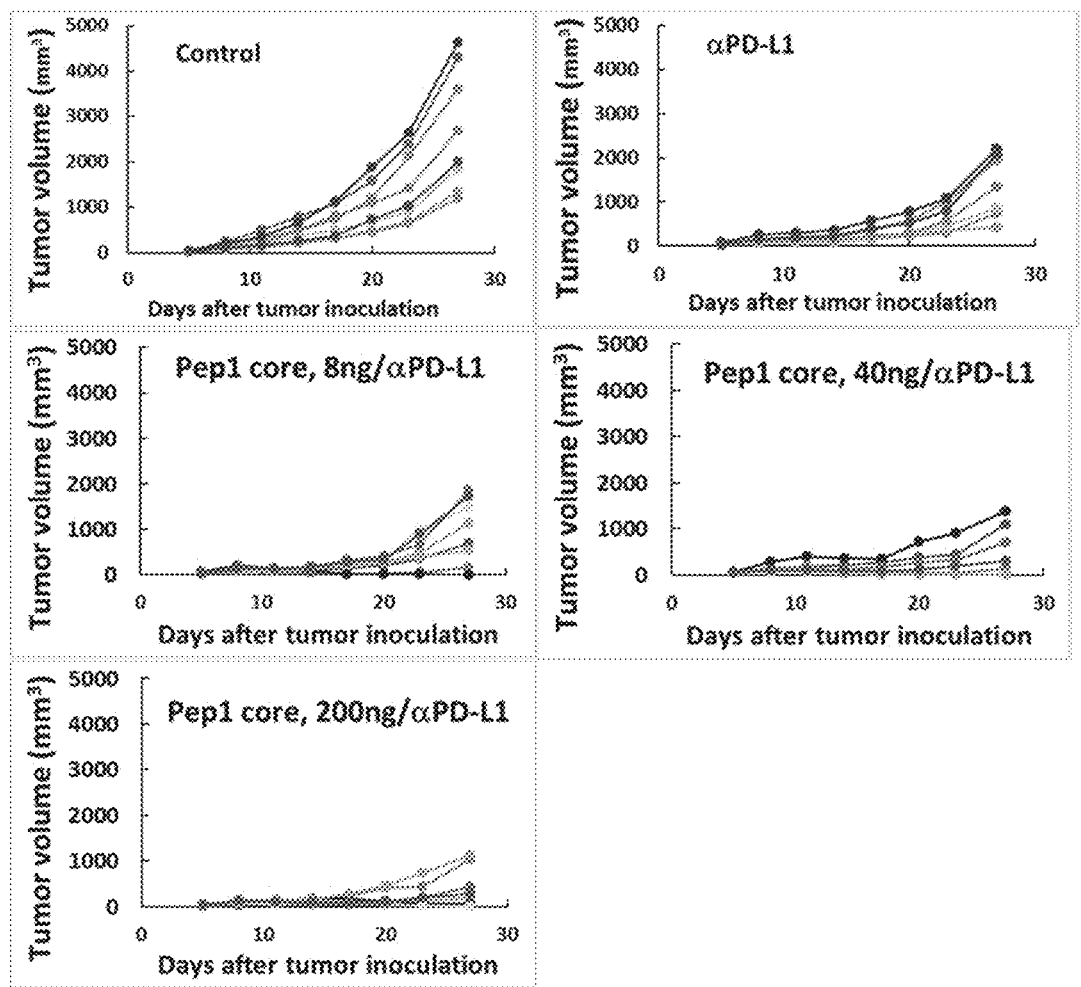
Figures 2, 7:
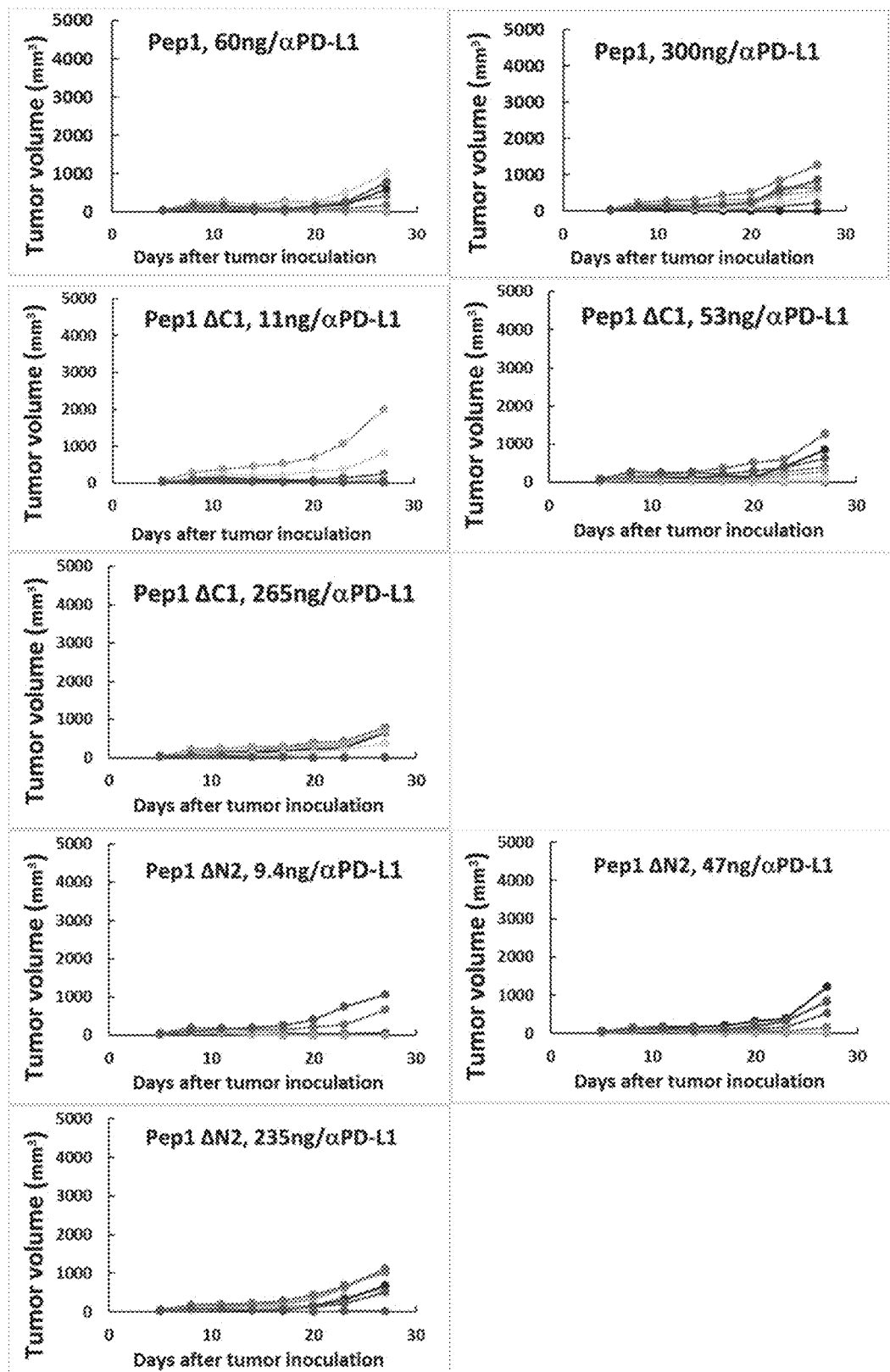

FIG. 7 shows time-dependent changes in tumor volume for each individual mouse. Pep1 used as a reference synergistically suppressed tumor growth when used in combination with the anti-PD-L1 antibody, and at doses of 60 ng and 300 ng, Colon26 solid tumor completely regressed in 5 to 7 of 8 mice. Even with the Pep1core, solid tumor growth was suppressed in a dose-dependent manner at doses of 8 to 200 ng/mouse, and 1 to 2 cases of complete regression of tumor were observed in groups of 8 mice. Pep1ΔC1 as a control showed complete regression of solid tumors at doses of 11 and 265 ng/mouse in 3 cases out of 8 cases, and showed complete regression in 1 case even at a dose of 53 ng. Pep1ΔN2 also showed a synergistic effect at the three doses administered, and in particular, solid tumors completely regressed at a dose of 9.4 ng/mouse in 4 cases out of 8 cases.

Figure 8:
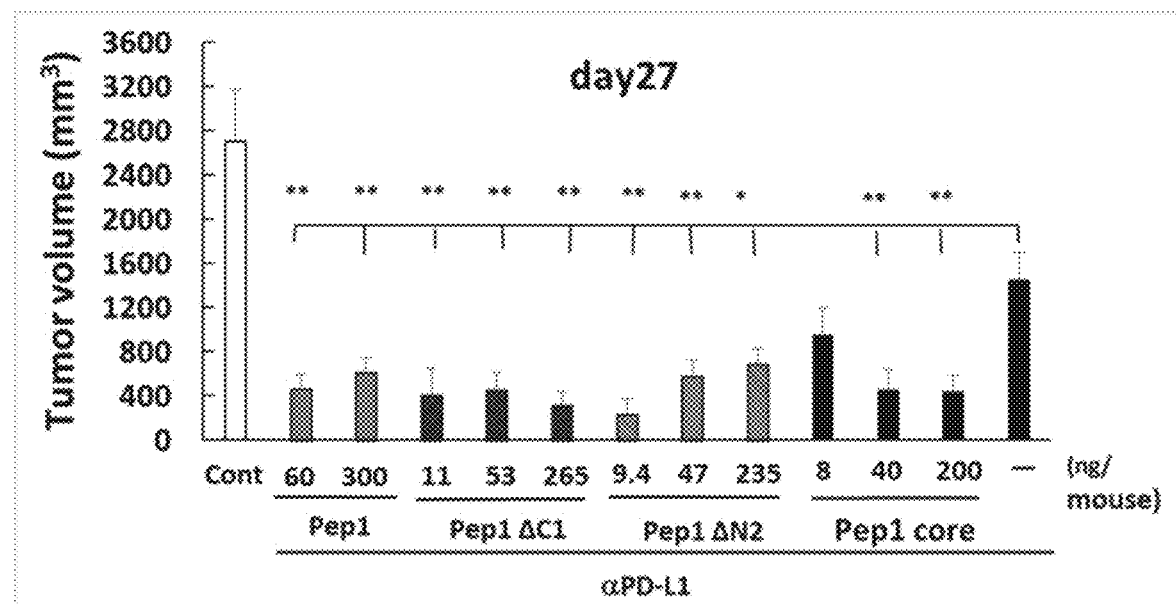
FIG. 8 shows measurement results of tumor volume 27 days after tumor cell implantation in each group of Colon26 tumor-bearing mice administered with Pep1, Pep1ΔC1, Pep1ΔN2, and Pep1core, each in combination with an anti-PD-L1 antibody (200 µg/mouse). Each peptide was administered at the dose shown in the figure. Significant difference from the anti-PD-L1 antibody single administration group *: p<0.05, **: p<0.01 (Dunnett).

FIG. 8 shows a result of comparing tumor volumes 27 days after tumor cell implantation between the administration groups (significant difference from the anti-PD-L1 antibody single administration group *: p<0.05, **: p<0.01 (Dunnett)). When used in combination with the anti-PD-L1 antibody, Pep1 synergistically significantly suppressed tumor growth. Pep1 ΔC1 as a control also synergistically significantly suppressed tumor growth, and the solid tumors completely regressed at doses of 11 and 265 ng/mouse in 3 cases out of 8 cases. Pep1ΔN2 also significantly suppressed tumor growth. The Pep1core also suppressed the growth of Colon26 solid tumors by the combined use with the anti-PD-L1 antibody, and a significant difference was observed with respect to the anti-PD-L1 antibody single administration group in the groups at doses of 40 and 200 ng/mouse.

From the results of FIGS. 7 and 8, it was revealed that EPKRR SARLSAKPPA KVEAKPKK (SEQ ID NO: 18) is the minimum active peptide of HMGN1.

The Pep1 mutant corresponding to the R→D mutant of Pep1 showed the same anti-tumor action as Pep1 (FIG. 6). RRSARLSA in NBD of HMGN1 is conserved in all HMGN proteins of various animals and is an important region for binding to nucleosomes, and it was revealed that the anti-tumor effect of the peptide was maintained even when all arginines (R) in this region are replaced by aspartic acids (D).

Further, in the HMGN1 protein sequence, a peptide consisting of a sequence of several residues shifted from the Pep1 region to the C-terminal side (PepO, KEEPKRR SARLSAKPPA KVEAKPKKAA AKDKSSDKK, SEQ ID NO: 10) was prepared, and the anti-tumor effect by the combined use with the anti-PD-L1 antibody was compared with that of the Pep1+anti-PD-L1 antibody combination. The amino acid sequence of PepO is a sequence described as the amino acid sequence of a functional fragment of an HMGN protein in U.S. Pat. No. 8,227,417 which discloses use of the HMGN protein for enhancing an antigen-specific immune reaction, and is an example of a known HMGN peptide.

Figure 9:
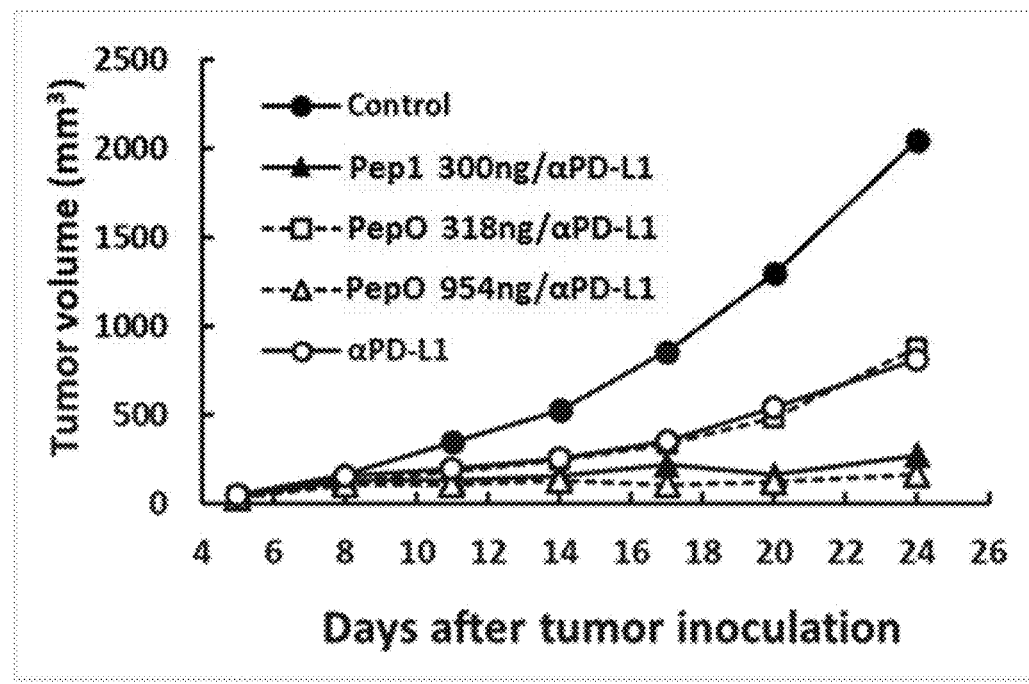
FIG. 9 shows a result of administering Pep1 (300 ng/mouse) and PepO (318 ng, 954 ng/mouse) to Colon26 tumor-bearing mice each in combination with an anti-PD-L1 antibody (200 µg/mouse), and measuring tumor volume over time.
Figure 10:
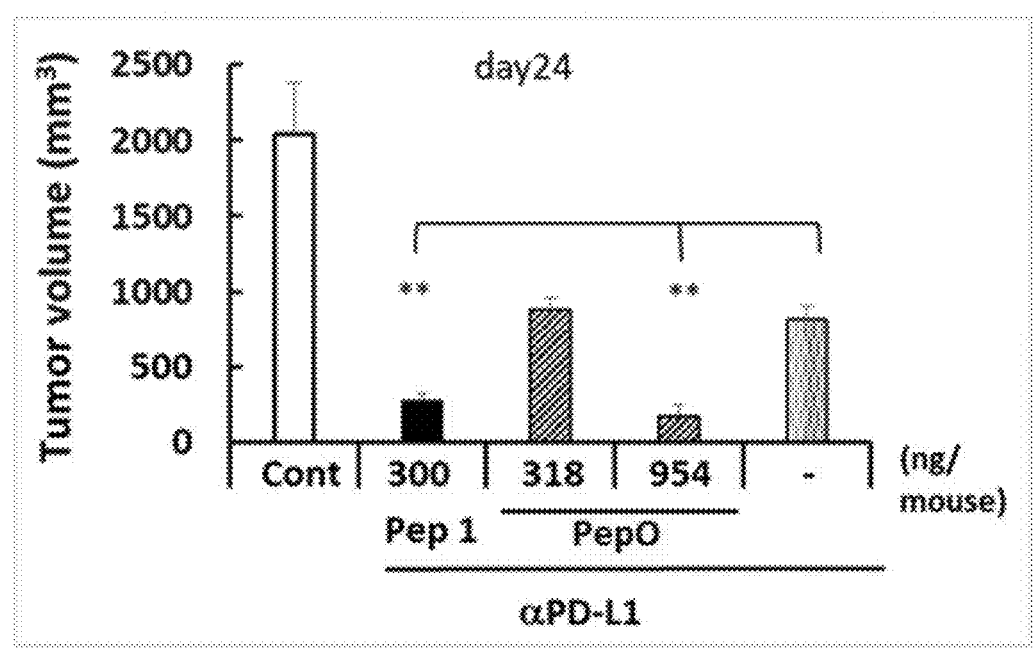
FIG. 10 shows measurement results of tumor volume 24 days after tumor cell implantation in the Pep1+anti-PD-L1 antibody combination group and the PepO+anti-PD-L1 antibody combination group. Each peptide was administered at the dose shown in the figure. The anti-PD-L1 antibody was administered at 200 µg/mouse. Significant difference from the anti-PD-1 antibody single administration group **: p<0.01 (Dunnett).

FIG. 9 shows a result of administering Pep1 or PepO to Colon26 tumor-bearing mice in combination with an anti-PD-L1 antibody (200 µg/mouse), and measuring tumor volume over time. FIG. 10 shows a result of measuring tumor volume 24 days after tumor implantation and comparing between the administration groups (significant difference from the anti-PD-1 antibody administration group **: p<0.01 (Dunnett)). The dose of Pep1 was set to 300 ng/mouse, and PepO was administered in an equimolar amount (318 ng/mouse) as or a triple amount (954 ng/mouse) of Pep1. PepO showed no anti-tumor effect when used in combination with the anti-PD-L1 antibody (200 μg/mouse) at a dose of 318 ng/mouse, but significantly suppressed tumor growth at the triple dose of 954 ng/mouse, and complete regression of solid tumors was observed in 3 mice.

As shown in FIG. 3, Pep1 was also effective when used in combination with the anti-PD-L1 antibody at 3 ng/mouse and 30 ng/mouse. Taken together with these results, it is considered that there is a 300 times or more potency difference in the anti-tumor action between PepO and Pep1 according to the present invention.

4. Anti-Tumor Effects of Partial Peptides of HMGN2, HMGN3, HMGN4 and HMGN5

It was investigated whether the NBD peptides of HMGN2, HMGN3, HMGN4, and HMGN5 also have anti-tumor effects. HMGN2 NBD-peptide (PepN2), HMGN3 NBD-peptide (PepN3), HMGN4 NBD-peptide (PepN4), and HMGN5 NBD-peptide (PepN5) were administered to Colon26 tumor-bearing mice in combination with the anti-PD-L1 antibody, and tumor volume was measured. Each peptide was administered to the mice at the same molar dose as 300 ng of Pep1.

Figure 11:
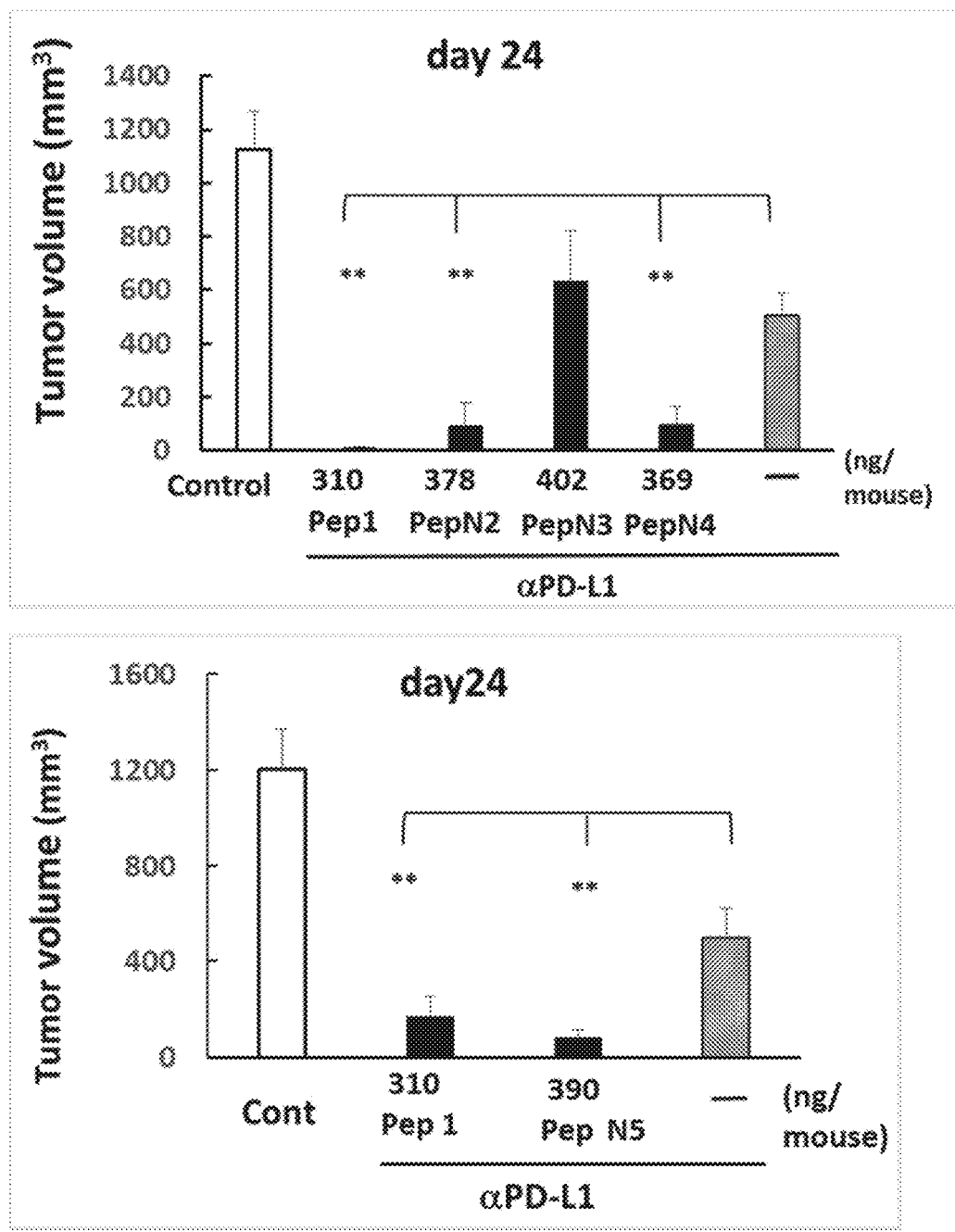
FIG. 11 shows a result of investigating anti-tumor effects of partial peptides of HMGN2, HMGN3, HMGN4, and HMGN5. Each partial peptide was administered to Colon26 tumor-bearing mice in combination with an anti-PD-L1 antibody, and tumor volumes measured 24 days after tumor implantation were compared between the anti-PD-L1 antibody single administration group and the combination administration groups. Significant difference from the anti-PD-L1 antibody single administration group **: p<0.01 (Dunnett).

FIG. 11 shows a result of comparing tumor volumes measured 24 days after tumor implantation between the anti-PD-L1 antibody single administration group and the combination administration groups. PepN2, PepN4 and PepN5 showed significant anti-tumor effects in combination with the anti-PD-L1 antibody (significant difference from the anti-PD-L1 antibody administration group **: p<0.01 (Dunnett)), and their anti-tumor effects were at the same level as Pep1. On the other hand, PepN3 showed no anti-tumor effect.

5. Anti-Tumor Effect by Combined Use of HMGN1 Partial Peptide and Anti-CD4 Antibody The partial peptide of human HMGN1, Pep1 (800 ng/mouse), was administered to Colon26 tumor-bearing mice in combination with an anti-CD4 antibody (200 μg/mouse), and the anti-tumor effect was investigated.

Figure 12:
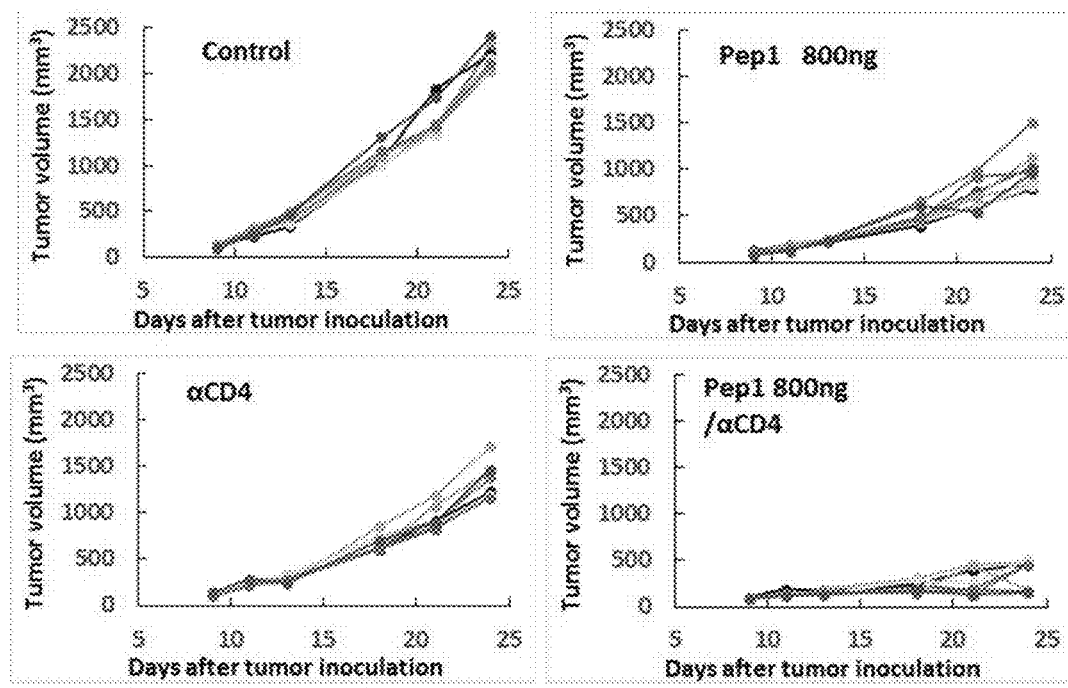
FIG. 12 shows a result of administering Pep1 (800 ng/mouse) to Colon26 tumor-bearing mice in combination with an anti-CD4 antibody (200 µg/mouse), and measuring tumor volume over time. The time-dependent change in the tumor volume for each individual mouse in each group are shown in graphs.
Figure 13:
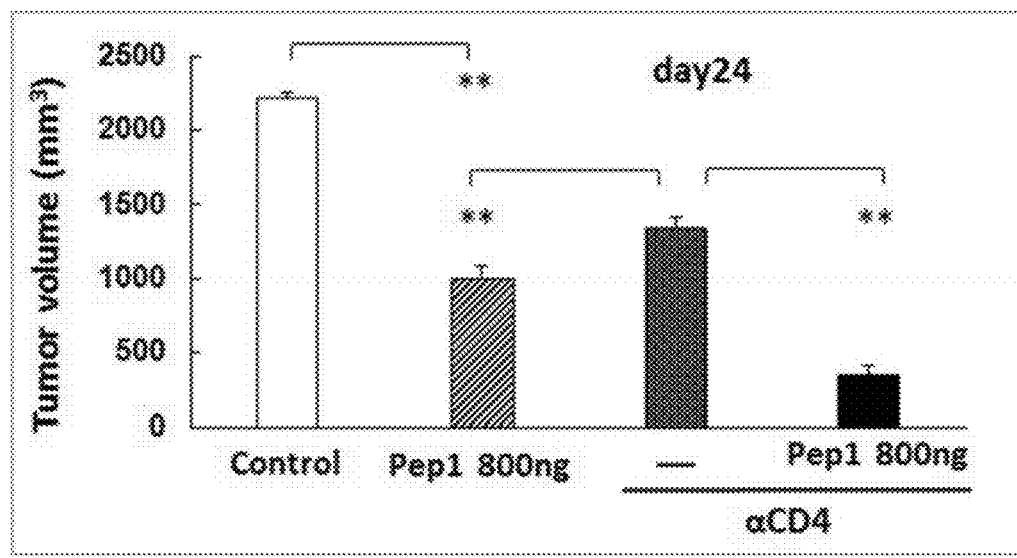
FIG. 13 shows measurement results of tumor volume 24 days after tumor cell implantation in the Pep1 single administration group, the anti-CD4 antibody single administration group, and the Pep1+anti-CD4 antibody combination group. ** indicates a significant difference between both groups, p<0.01 (Dunnett).

FIG. 12 shows time-dependent changes in tumor volume for each individual mouse. FIG. 13 shows a result of measuring tumor volume 24 days after tumor implantation and comparing between the administration groups (** indicates a significant difference between both groups, p<0.01 (Dunnett)). Pep1 synergistically suppressed Colon26 solid tumor growth even when used in combination with the anti-CD4 antibody, as in the case of combined use with the anti-PD-L1 antibody.

The invention claimed is:

1. A method of treating cancer, comprising administering to a patient in need of treatment of cancer an effective amount of an anti-cancer agent containing an amino acid sequence of a peptide consisting of an amino acid sequence selected from the sequences (1) to (5) and (7) to (9):

(1)
            (SEQ ID NO: 3)
SSAE GAAKEEPKRR SARLSAKPPA KVEAKPKKAA AKD (2) an amino acid sequence in which 1 to 8 amino acid residues at the C terminus are deleted in the sequence (1)

(3) an amino acid sequence in which 1 to 13 amino acid residues at the N terminus are deleted in the sequence (1)

(4) an amino acid sequence in which 1 to 13 amino acid residues at the N terminus are deleted in the sequence (2)

(5)
            (SEQ ID NO: 12)
EGDAKGDK AKVKDEPQRR SARLSAKPA PPKPEPKPKKAPAKKGE (7)
            (SEQ ID NO: 15)
GQG DMRQEPKRR SARLSAMLV PVTPEVKPKRTSSSRKMKTKSD (8) an amino acid sequence in which 1 to 5 amino acid residues at the C terminus and/or 1 to 5 amino acid residues at the N terminus are deleted in any one of the sequences (5) and (7)

(9) an amino acid sequence in which 1 to 3 amino acid residues are substituted in any one of the sequences (1) to (5) or (7) to (8).

2. The method according to claim 1, wherein the sequence (2) is an amino acid sequence in which 1 to 5 amino acid residues at the C terminus are deleted in the sequence (1), the sequence (3) is an amino acid sequence in which 1 to 9 amino acid residues at the N terminus are deleted in the sequence (1), and the sequence (4) is an amino acid sequence in which 1 to 9 amino acid residues at the N terminus are deleted in the sequence (2).

3. The method according to claim 1, wherein the amino acid sequence is represented by any one of the sequences (1) to (5) or (7).

4. The method according to claim 1, wherein the amino acid sequence is represented by any one of the sequences (1) to (4).

5. The method according to claim 1, wherein the sequence (2) is SSAE GAAKEEPKRR SARLSAKPPA KVEAKPKK (SEQ ID NO: 5), the sequence (3) is AAKEEPKRR SARLSAKPPA KVEAKPKKAA AKD (SEQ ID NO: 7) or EPKRR SARLSAKPPA KVEAKPKKAA AKD (SEQ ID NO: 8), and the sequence (4) is EPKRR SARLSAKPPA KVEAKPKK (SEQ ID NO: 18).

6. The method according to claim 1, wherein the amino acid sequence is represented by an amino acid sequence selected from the group consisting of SEQ ID NO: 3, SEQ ID NO: 5, SEQ ID NO: 7, SEQ ID NO: 8, SEQ ID NO: 12, SEQ ID NO: 15, and SEQ ID NO: 18.

7. The method according to claim 1, wherein the cancer is a solid cancer.

8. A method of enhancing the effect of an anti-cancer agent, comprising administering to a subject in need thereof an effective amount of an agent containing an amino acid sequence of a peptide consisting of an amino acid sequence selected from the sequences (1) to (5) and (7) to (9):

(1)
                                            (SEQ ID NO: 3)
SSAE GAAKEEPKRR SARLSAKPPA KVEAKPKKAA AKD (2) an amino acid sequence in which 1 to 8 amino acid residues at the C terminus are deleted in the sequence (1)

(3) an amino acid sequence in which 1 to 13 amino acid residues at the N terminus are deleted in the sequence (1)

(4) an amino acid sequence in which 1 to 13 amino acid residues at the N terminus are deleted in the sequence (2)

(5)
                                            (SEQ ID NO: 12)
EGDAKGDK AKVKDEPQRR SARLSAKPA PPKPEPKPKKAPAKKGE (7)
                                            (SEQ ID NO: 15)
GQG DMRQEPKRR SARLSAMLV PVTPEVKPKRTSSSRKMKTKSD (8) an amino acid sequence in which 1 to 5 amino acid residues at the C terminus and/or 1 to 5 amino acid residues at the N terminus are deleted in any one of the sequences (5) and (7)

(9) an amino acid sequence in which 1 to 3 amino acid residues are substituted in any one of the sequences (1) to (5) or (7) to (8).

9. The method according to claim 8, wherein the sequence (2) is an amino acid sequence in which 1 to 5 amino acid residues at the C terminus are deleted in the sequence (1), the sequence (3) is an amino acid sequence in which 1 to 9 amino acid residues at the N terminus are deleted in the sequence (1), and the sequence (4) is an amino acid sequence in which 1 to 9 amino acid residues at the N terminus are deleted in the sequence (2).

10. The method according to claim 8, wherein the amino acid sequence is represented by any one of the sequences (1) to (5) or (7).

11. The method according to claim 8, wherein the amino acid sequence is represented by any one of the sequences (1) to (4).

12. The method according to claim 8, wherein the sequence (2) is SSAE GAAKEEPKRR SARLSAKPPA KVEAKPKK (SEQ ID NO: 5), the sequence (3) is AAKEEPKRR SARLSAKPPA KVEAKPKKAA AKD (SEQ ID NO: 7) or EPKRR SARLSAKPPA KVEAKPKKAA AKD (SEQ ID NO: 8), and the sequence (4) is EPKRR SARLSAKPPA KVEAKPKK (SEQ ID NO: 18).

13. The method according to claim 8, wherein the amino acid sequence is represented by an amino acid sequence selected from the group consisting of SEQ ID NO: 3, SEQ ID NO: 5, SEQ ID NO: 7, SEQ ID NO: 8, SEQ ID NO: 12, SEQ ID NO: 15, and SEQ ID NO: 18.

14. The method according to claim 8, wherein the anti-cancer agent is an anti-cancer agent containing at least one member selected from the group consisting of an immune checkpoint regulator and an anti-CD4 antibody or antigen-binding fragment thereof.

15. The method according to claim 14, wherein the immune checkpoint regulator is at least one member selected from the group consisting of an antagonist against an inhibitory immune checkpoint molecule, and an agonist against a co-stimulatory immune checkpoint molecule.

16. The method according to claim 15, wherein the immune checkpoint regulator is at least one anti-immune checkpoint antibody.

17. The method according to claim 16, wherein the anti-immune checkpoint antibody is at least one member selected from the group consisting of an antagonistic anti-PD-1 antibody, an anti-PD-L1 antibody, and an anti-PD-L2 antibody.

18. The method according to claim 14, wherein the anti-CD4 antibody or antigen-binding fragment thereof is an anti-CD4 antibody having cytotoxic activity, or an anti-CD4 antibody or antigen-binding fragment thereof to which a cytotoxic component is bound.

* * * * *